US008958612B2

(12) United States Patent
Miyasa et al.

(10) Patent No.: US 8,958,612 B2
(45) Date of Patent: Feb. 17, 2015

(54) INFORMATION PROCESSING APPARATUS AND INFORMATION PROCESSING METHOD

(75) Inventors: Kazuhiro Miyasa, Yokohama (JP); Kenji Morita, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/424,550

(22) Filed: Mar. 20, 2012

(65) Prior Publication Data

US 2012/0250959 A1 Oct. 4, 2012

Related U.S. Application Data

(63) Continuation of application No. 12/778,830, filed on May 12, 2010, now Pat. No. 8,160,333, which is a continuation of application No. PCT/JP2009/005345, filed on Oct. 14, 2009.

(30) Foreign Application Priority Data

Jan. 14, 2009 (JP) .................................. 2009-006117

(51) Int. Cl.
*G06K 9/00* (2006.01)
*G06F 19/00* (2011.01)
*G06T 7/00* (2006.01)

(52) U.S. Cl.
CPC .......... *G06F 19/321* (2013.01); *G06F 19/3437* (2013.01); *G06F 19/3443* (2013.01); *G06T 7/0016* (2013.01); *G06T 2207/30004* (2013.01)
USPC ....................................................... 382/128

(58) Field of Classification Search
None
See application file for complete search history.

(56) References Cited

U.S. PATENT DOCUMENTS

| 6,849,048 | B2 * | 2/2005 | Omiya ........................ 600/443 |
| 6,925,199 | B2 * | 8/2005 | Murao ......................... 382/131 |
| 7,552,062 | B2 | 6/2009 | Bito et al. | |
| 7,616,793 | B2 * | 11/2009 | Marshall et al. ............. 382/128 |
| 7,949,166 | B2 | 5/2011 | Moriya et al. | |

(Continued)

FOREIGN PATENT DOCUMENTS

| JP | 2004-173748 A | 6/2004 |
| JP | 2007-287018 A | 11/2007 |

(Continued)

OTHER PUBLICATIONS

Japanese Office Action issued in corresponding application No. 2013-144853 on Apr. 21, 2014.

*Primary Examiner* — Nancy Bitar
(74) *Attorney, Agent, or Firm* — Carter, DeLuca, Farrell & Schmidt, LLP

(57) ABSTRACT

This invention is directed to appropriately searching for case data similar in the process of a disease. A similar case search apparatus (100) according to this invention includes a disease progress model building function of building a disease progress model by extracting feature amounts from a plurality of medical images obtained by imaging the same object in different periods, a unit configured to read out case data, a unit configured to acquire inspection data, a similar case search function of interpolating, by using the model, feature amounts extracted from the plurality of medical images contained in the inspection data, and calculate a similarity between the inspection data and the case data by using the interpolated feature amounts, and a monitor (111) which displays case data selected based on the calculated similarity.

19 Claims, 12 Drawing Sheets

(56) References Cited

U.S. PATENT DOCUMENTS

| | | |
|---|---|---|
| 8,065,166 B2 | 11/2011 | Maresh et al. |
| 8,160,333 B2 * | 4/2012 | Miyasa et al. ............. 382/128 |
| 8,189,883 B2 * | 5/2012 | Oosawa et al. ............. 382/128 |
| 2003/0048265 A1 * | 3/2003 | Bito et al. ............. 345/419 |
| 2006/0025671 A1 * | 2/2006 | Kusunoki ............. 600/407 |
| 2008/0212856 A1 * | 9/2008 | Oosawa et al. ............. 382/128 |
| 2009/0080734 A1 * | 3/2009 | Moriya et al. ............. 382/128 |
| 2009/0313242 A1 * | 12/2009 | Kodama ............. 707/5 |
| 2010/0226550 A1 * | 9/2010 | Miyasa et al. ............. 382/128 |
| 2011/0007940 A1 * | 1/2011 | Hamza et al. ............. 382/103 |

FOREIGN PATENT DOCUMENTS

| | | |
|---|---|---|
| JP | 2007-325641 A | 12/2007 |
| JP | 2008-217362 A | 9/2008 |
| JP | 5317716 B | 10/2013 |

* cited by examiner

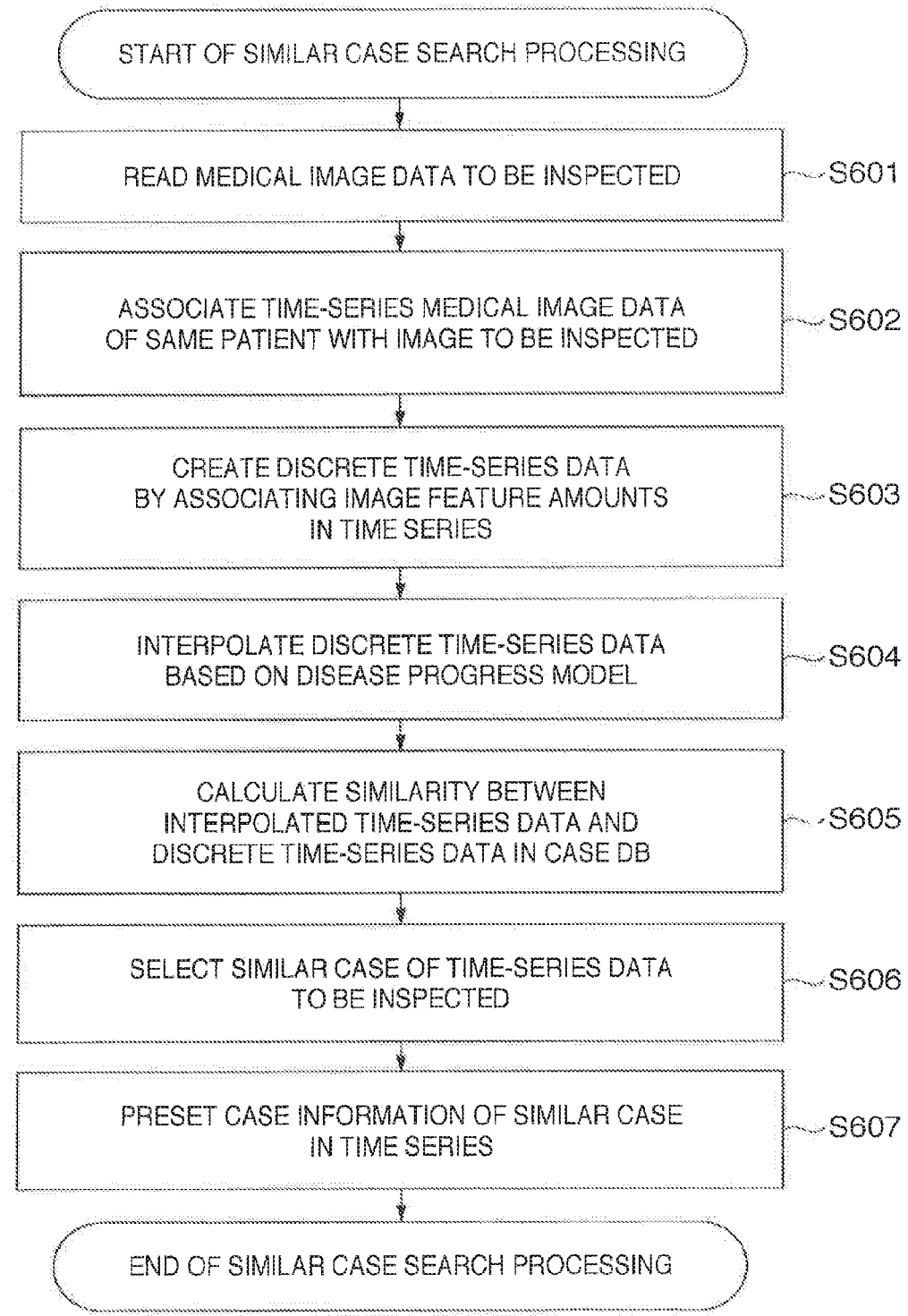

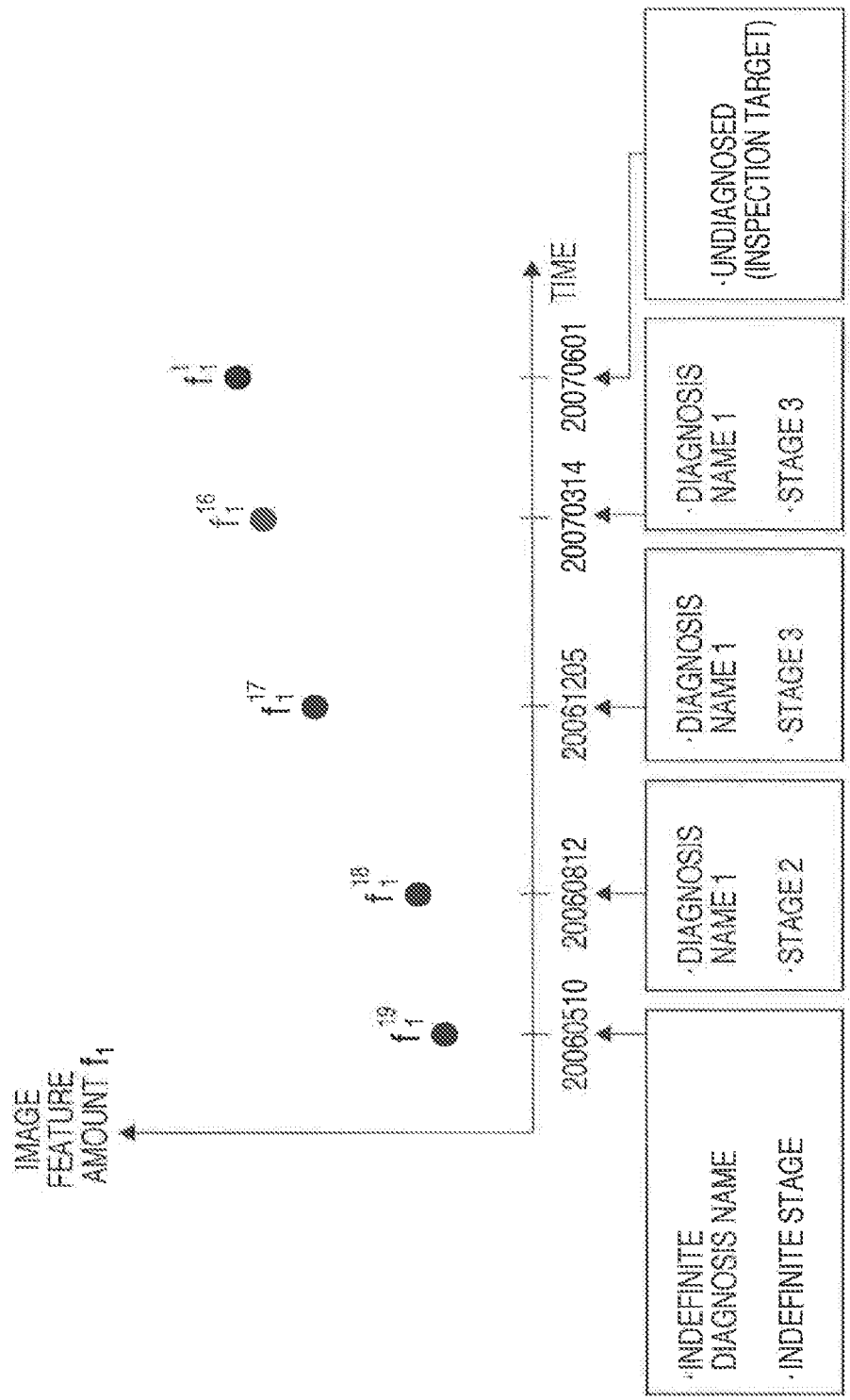

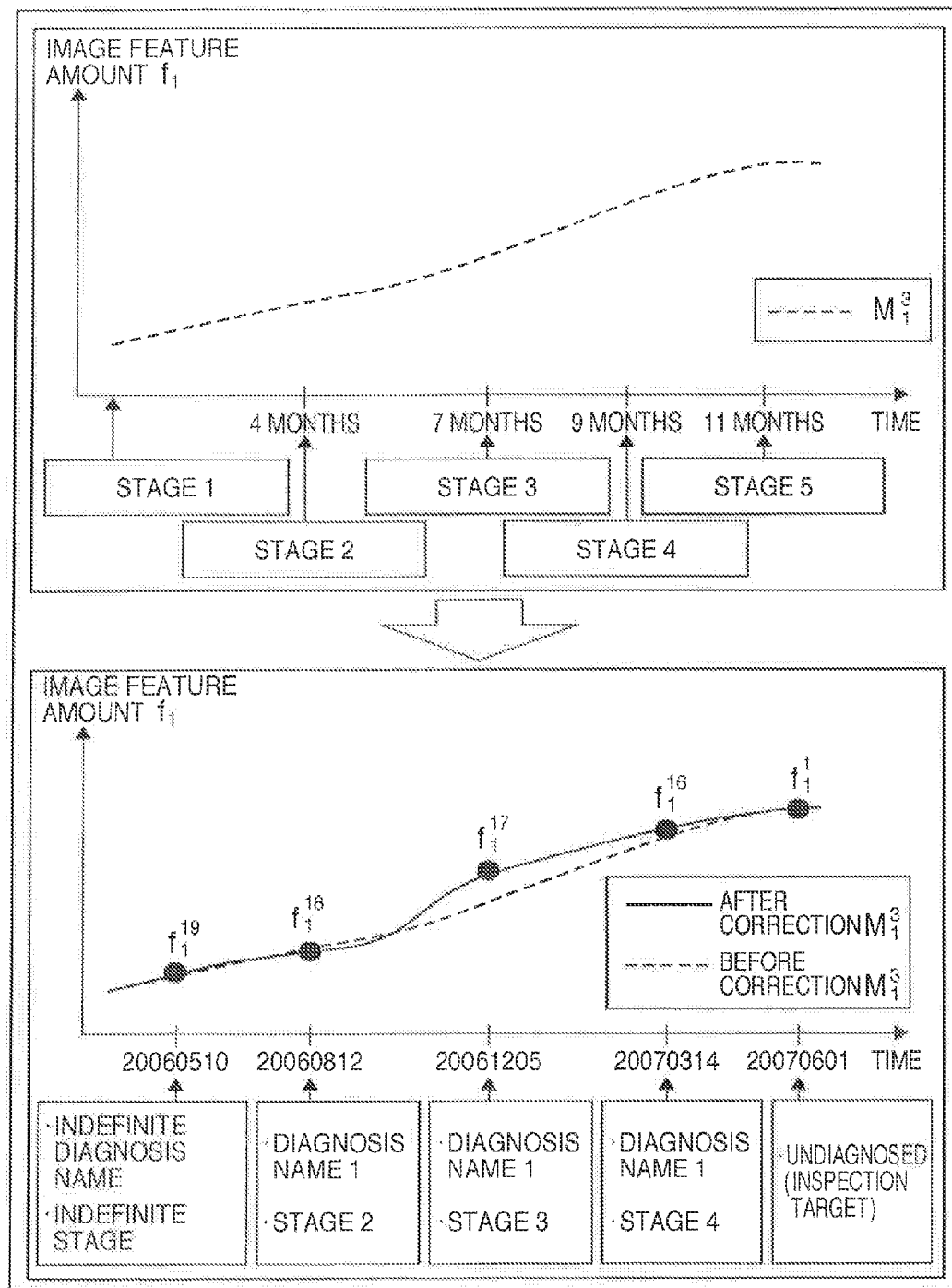

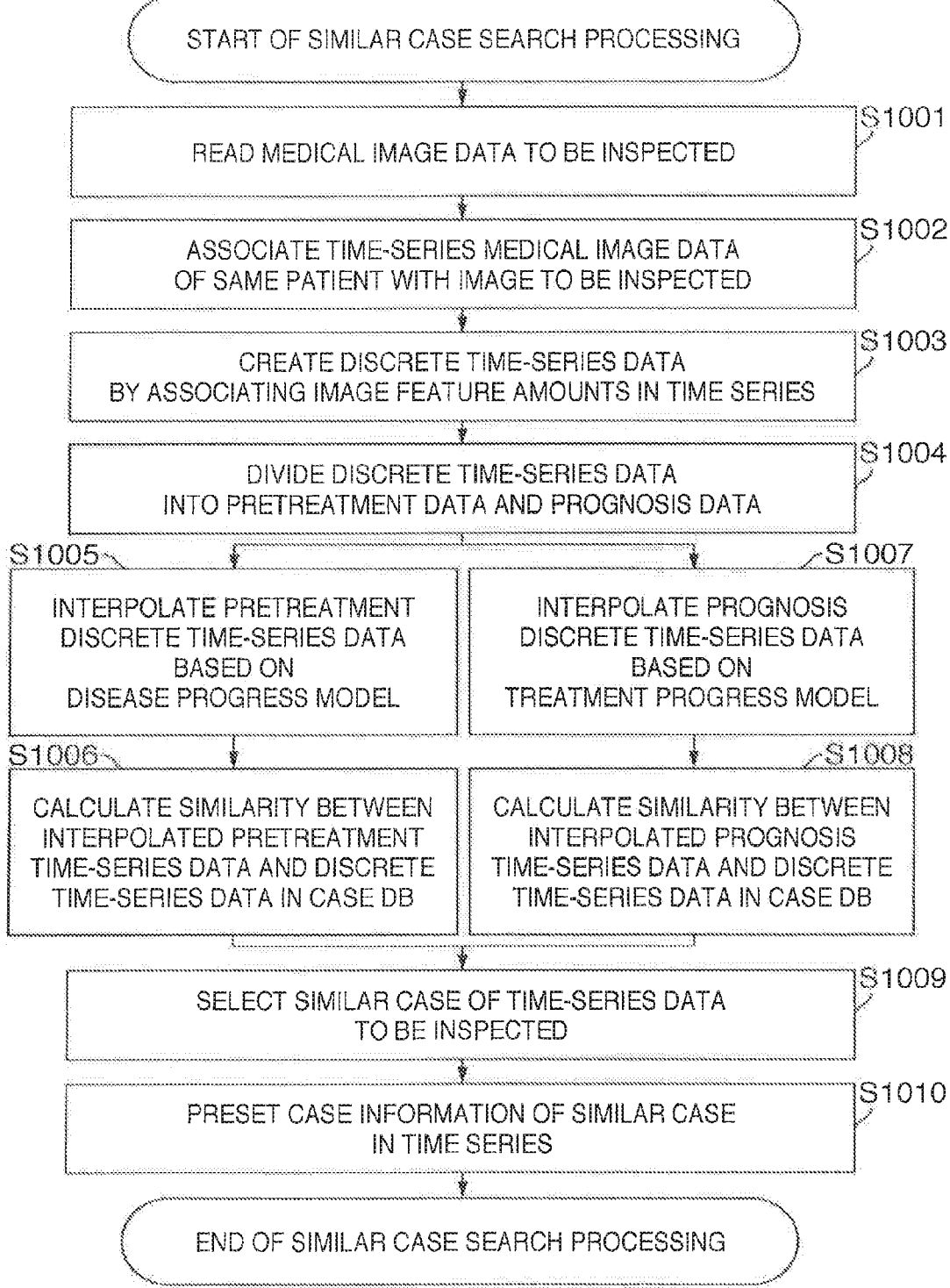

INFORMATION PROCESSING APPARATUS AND INFORMATION PROCESSING METHOD

TECHNICAL FIELD

The present invention relates to an information processing technique for searching for similar case data.

BACKGROUND ART

Medical documents and medical images are becoming digital along with recent popularization of medical information systems including HIS and PACS. HIS stands for a hospital information system, and PACS stands for a picture archiving and communication system.

Medical images (e.g., X-ray image, CT image, and MRI image), which were often viewed on a film viewer after developed on films, are digitized now and can be viewed on a monitor.

More specifically, digital medical images (medical image data) can be stored in the PACS or the like, and if necessary, read out from it and interpreted on the monitor of an image interpretation terminal.

Medical documents such as a medical record are also being digitized as medical record data. Medical record data of a patient serving as an object can be read out from the HIS or the like and viewed on the monitor of an image interpretation terminal.

In the digital environment, an image interpreter can receive an image interpretation request form by a digital message. Based on the message, he reads out medical image data of a patient from the PACS and makes a diagnosis while displaying it on the image interpretation monitor of an image interpretation terminal. If necessary, the image interpreter reads out medical record data of the patient from the HIS and makes a diagnosis while displaying it on another monitor.

A desire to reduce the burden on an image interpreter in image interpretation has urged the development of medical image processing apparatuses. This apparatus makes a computer-aided diagnosis by analyzing medical image data to automatically detect a morbid portion or the like. Computer-aided diagnosis will be referred to as CAD.

CAD can automatically detect an abnormal shadow candidate as a morbid portion and display it. More specifically, a computer can process medical image data such as an X-ray image to detect and display an abnormal tumor shadow or high-density small calcified shadow caused by a cancer or the like. The use of CAD can reduce the burden on an image interpreter in image interpretation and increase the image interpretation accuracy.

Another technique for reducing the burden on an image interpreter in image interpretation is disclosed in, for example, patent reference 1 listed below. The technique in patent reference 1 can automatically detect an abnormal candidate from medical image data and automatically set a region (to be referred to as a region of interest) containing the abnormal candidate portion. This technique can save an image interpreter from having to manually set a region of interest.

Demand has also arisen for developing a technique for further increasing the image interpretation accuracy by an image interpreter in image interpretation. Generally when interpreting medical image data to make a diagnosis, an image interpreter sometimes hesitates to decide a diagnosis name if a morbid portion in the medical image data during interpretation has an unfamiliar image feature or there are a plurality of morbid portions having similar image features.

In this case, the image interpreter at a loss may ask advice for another experienced image interpreter, or refer to documents such as medical books and read the description of an image feature regarding a suspicious disease name. Alternatively, he may examine illustrated medical documents to locate a photo similar to a morbid portion captured in the medical image data during image interpretation, and read a disease name corresponding to the photo for reference of the diagnosis.

However, the image interpreter may not always have an advisory experienced image interpreter. Even if the image interpreter examines medical documents, he may not be able to locate a photo similar to a morbid portion captured in the medical image data during image interpretation, or the description of an image feature.

To solve this problem by a digital means and increase the image interpretation accuracy, similar case search apparatuses have been developed recently. The basic idea of the similar case search apparatus is to support a diagnosis by searching for a plurality of case data from those accumulated in the past based on any criterion and presenting them to an image interpreter.

As a general method in similar case search, it is known to search an image database accumulated in the past for image data similar in image feature amount to medical image data during image interpretation.

Diagnosis is sometimes made based on the result of follow-up such as the progress of a disease. In this case, the similarity of medical image data at one time point is determined. Also, the similarity of the process is determined based on a plurality of medical image data obtained by imaging the same patient in different periods. By presenting case data similar in process, this method can present highly reliable reference information in disease diagnosing, subsequent inspection planning, treatment planning, and the like.

For example, patent reference 2 listed below discloses a similar case search method which assists a diagnosis by determining the similarity of the process based on a plurality of medical image data obtained by imaging the same patient in different periods.

According to patent reference 2, case data which are similar in image feature amount to respective time-series medical image data to be inspected and are equal in imaging time interval to them can be presented as case data similar in the process of a disease.

PRIOR ART REFERENCES

Patent References

Patent Reference 1: Japanese Patent Laid-Open No. 2007-325641

Patent Reference 2: Japanese Patent Laid-Open No. 2007-287018

However, according to the invention disclosed in patent reference 2, only case data equal in imaging time interval to time-series medical image data to be inspected can be presented as a case data candidate similar in process.

In other words, case data different in imaging time interval from time-series medical image data to be inspected cannot be presented as similar case data even if the actual process is similar.

To increase the image interpretation accuracy, it is desirable to appropriately search for case data similar in process regardless of the imaging time interval.

The present invention has been made to overcome the conventional problems.

SUMMARY OF THE INVENTION

An information processing apparatus according to the present invention has the following arrangement. That is, an information processing apparatus comprises a building unit configured to build a temporal feature amount change model by extracting feature amounts from a plurality of medical images obtained by imaging the same object in different periods, a readout unit configured to read out, from a database, case data containing a plurality of medical images obtained by imaging the same object in different periods, an acquisition unit configured to acquire inspection data containing a plurality of medical images obtained by imaging an object to be inspected in different periods, an interpolation unit configured to interpolate, by using the model, either of feature amounts extracted from the plurality of medical images contained in the case data and feature amounts extracted from the plurality of medical images contained in the inspection data, a calculation unit configured to calculate similarities between the plurality of medical images contained in the inspection data and the plurality of medical images contained in the case data by using the feature amounts interpolated by the interpolation unit, and an output unit configured to output case data selected based on the calculated similarities.

The present invention can appropriately search for case data similar in process.

Other features and advantages of the present invention will become apparent from the following description of exemplary embodiments with reference to the accompanying drawings. Note that the same reference numerals denote the same or similar parts throughout the accompanying drawings.

BRIEF DESCRIPTION OF DRAWINGS

FIG. 6 is a flowchart showing the sequence of similar case search processing;

FIG. 7 is a graph of discrete time-series data;

FIG. 8 is a graph of interpolated discrete time-series data;

FIG. 10 is a flowchart showing the sequence of similar case search processing;

DETAILED DESCRIPTION OF THE EMBODIMENTS

Preferred embodiments of the present invention will now be described with reference to the drawings.

First Embodiment

<1. Overall Configuration of Medical Information System and Arrangement of Similar Case Search Apparatus>

Figure 1:
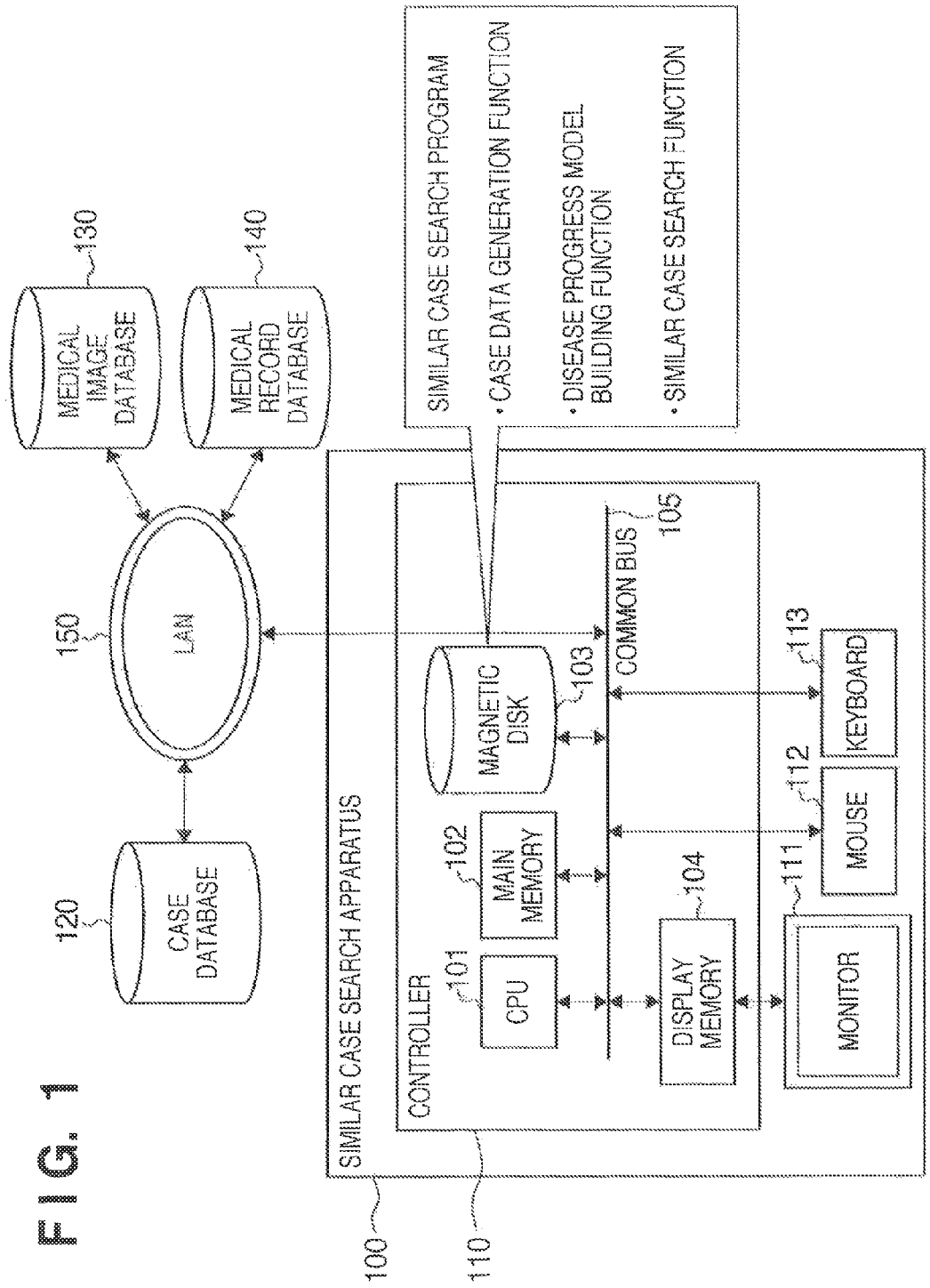
FIG. 1 is a block diagram showing the overall configuration of a medical information system having a similar case search apparatus (information processing apparatus) and the arrangement of the similar case search apparatus according to the first embodiment of the present invention.

FIG. 1 is a block diagram showing the overall configuration of a medical information system having a similar case search apparatus (information processing apparatus) and the arrangement of the similar case search apparatus according to the first embodiment of the present invention.

In FIG. 1, a similar case search apparatus 100 includes a controller 110, monitor 111, mouse 112, and keyboard 113.

The controller 110 includes a central processing unit (CPU) 101, main memory 102, magnetic disk 103, display memory 104, and common bus 105. The CPU 101 executes control programs stored in the main memory 102 to achieve various control operations such as communication with a case database 120, medical image database 130, and medical record database 140 and control of the overall similar case search apparatus 100.

The CPU 101 executes a control program for controlling the operation of each building component of the similar case search apparatus 100, and a similar case search program which is the main function of the apparatus. The main memory 102 stores control programs to be executed by the CPU 101, and provides a work area when the CPU 101 executes the similar case search program.

The magnetic disk 103 stores control programs such as an operating system (OS) and device drivers for peripheral devices. In addition, the magnetic disk 103 stores the similar case search program for implementing a case data generation function, disease progress model building function, and similar case search function (to be described later). The magnetic disk 103 further stores various kinds of data used by the similar case search program.

The display memory 104 temporarily stores display data for the monitor 111. The monitor 111 is, for example, a CRT monitor or liquid crystal monitor, and displays an image based on display data output from the display memory 104.

The mouse 112 and keyboard 113 are building components used when the user performs pointing input or inputs text or the like. The common bus 105 connects these building components so that they can communicate with each other.

Note that the configuration of the medical information system is not limited to the configuration example of FIG. 1. For example, an existing PACS is usable as the medical image database 130. An electronic medical record system, which is a subsystem of an existing HIS, is available as the medical record database 140.

It is also possible to connect external storage devices, for example, an FDD, HDD, CD drive, DVD drive, MO drive, and ZIP drive to the similar case search apparatus 100 and read case data, medical image data, and medical record data from these drives.

By building the medical information system, the similar case search apparatus 100 can read out case data from the case database 120 via a LAN 150. Also, the similar case search apparatus 100 can read out medical image data from the medical image database 130 and medical record data from the medical record database 140.

Note that "medical image data" stored in the medical image database 130 include a simple X-ray image (roentgenogram), X-ray CT image, MRI image, PET image, SPECT image, and ultrasonic image.

"Medical record data" stored in the medical record database 140 describes personal information (e.g., name, birth date, age, and sex) and clinical information (e.g., various test values, chief complaint, past history, and treatment history) of a patient serving as an object. The "medical record data" further includes reference information to patient's medical image data stored in the medical image database 130, and finding information of a doctor in charge. After making a diagnosis, the medical record data also includes a definite diagnosis name.

"Case data" stored in the case database 120 is information which associates medical image data obtained by imaging the same patient in different periods, corresponding medical record data, and data obtained by analyzing time-series medical image data.

The case data generation function in the similar case search program of the similar case search apparatus 100 is executed to generate case data and store it in the case database 120. More specifically, case data is generated as a copy of some of medical image data archived in the medical image database 130 and medical record data archived in the medical record database 140, or as link information to these data. The generated case data is then stored.

Table 1 exemplifies a case data table stored in the case database 120. The case data table is a set of case data which are formed from the same items and arranged regularly. In Table 1, medical image data of the same patient are associated by the same case data ID (equivalent to a patient ID).

The similar case search apparatus 100 according to the first embodiment generates case data and then executes the similar case search function. More specifically, the similar case search apparatus 100 searches the case database 120 for case data similar in process by using, as a query, information (to be referred to as a case to be inspected) which is a combination of medical image data (to be referred to as an image to be inspected) of a patient to be inspected and past time-series medical image data of the patient.

At this time, the similarity between a case to be inspected and case data having a different imaging time interval can be calculated by interpolating time-series data (to be referred to as discrete time-series data) which are discrete for the image feature amount of the case to be inspected. The method of interpolating discrete time-series data of a case to be inspected can use, for example, other medical image data which are partially equal in imaging time interval to a case to be inspected and have similar medical image data.

However, it is difficult to interpolate the image feature amount of a case to be inspected and generate successive time-series data by using medical image data contained in case data. According to the first embodiment, therefore, when executing the similar case search function, the disease progress model building function is operated to first create a plurality of models (temporal image feature amount change models) by averaging successive time-series progress patterns of a disease. Then, one of the created average disease progress models that best matches the case to be inspected is selected. The selected average disease progress model is applied to discrete time-series data unique to the case to be inspected, thereby performing interpolation for generating

TABLE 1

| Case Data ID (Patient ID) | Definite Diagnosis Name | Stage of Disease | Reference Intermediate to Medical Record Data | Imaging Date | Image Type | Target Organ | Reference Information to Image Data | Slice Number of Interest | Coordinate Information of Region of Interest (X0, Y0, X1, Y1) | Image Feature Amount Fk of Region of Interest |
|---|---|---|---|---|---|---|---|---|---|---|
| 1 | Diagnosis name 1 | 4 | ... | 20070501 | Contrast enhanced CT | Lung | ... | 21 | (112, 263, 193, 335) | F1 |
|   | Diagnosis name 1 | 3 | ... | 20070301 | Contrast enhanced CT | Lung | ... | 23 | (115, 260, 195, 340) | F2 |
|   | Diagnosis name 1 | 2 | ... | 20070109 | Contrast enhanced CT | Lung | ... | 26 | (110, 258, 188, 343) | F3 |
|   | Diagnosis name 1 | 2 | ... | 20070905 | Contrast enhanced CT | Lung | ... | 22 | (113, 262, 190, 338) | F4 |
|   | Indefinite |   | ... | 20070510 | Contrast enhanced CT | Lung | ... | 22 | (112, 260, 186, 341) | F5 |
| 2 | Diagnosis name 6 | 5 | ... | 20070512 | Contrast enhanced CT | Lung | ... | 52 | (167, 258, 205, 292) | F6 |
|   | Diagnosis name 6 | 5 | ... | 20070210 | Contrast enhanced CT | Lung | ... | 57 | (170, 248, 209, 295) | F7 |
|   | Diagnosis name 6 | 4 | ... | 20061106 | Contrast enhanced CT | Lung | ... | 54 | (171, 251, 208, 290) | F8 |
|   | Diagnosis name 6 | 4 | ... | 20060706 | Contrast enhanced CT | Lung | ... | 50 | (166, 249, 210, 293) | F9 |
| 3 | Diagnosis name 3 | 4 | ... | 20070516 | Plain CT | Lung | ... | 17 | (310, 219, 335, 254) | F10 |
|   | Diagnosis name 3 | 3 | ... | 20070410 | Plain CT | Lung | ... | 19 | (315, 222, 340, 250) | F11 |
|   | Diagnosis name 3 | 3 | ... | 20070315 | Plain CT | Lung | ... | 21 | (308, 215, 332, 259) | F12 |
|   | Diagnosis name 3 | 2 | ... | 20070108 | Plain CT | Lung | ... | 20 | (312, 225, 334, 248) | F13 |
|   | Diagnosis name 3 | 2 | ... | 20061125 | Plain CT | Lung | ... | 19 | (307, 212, 340, 251) | F14 |
|   | Indefinite |   | ... | 20060812 | Plain CT | Lung | ... | 18 | (313, 218, 336, 253) | F15 |
| ... | ... | ... | ... | ... | ... | ... | ... | ... | ... | ... | successive time-series data. A plurality of created models will be called "disease progress models".

Details of the functions (case data generation function, disease progress model building function, and similar case search function) implemented by the similar case search program will be described.

<2. Case Data Generation Function>

Details of the case data generation function will be explained with reference to the flowchart of FIG. 2. A case will be described, in which time-series medical image data of the same patient are saved in association with image feature amounts extracted from them, and medical record data, as represented in Table 1.

In step S201, the CPU 101 reads out medical image data (to be referred to as an image to be stored) to be stored in the case database 120 from the medical image database 130 in accordance with an input from the mouse 112 or keyboard 113. The CPU 101 inputs the readout image to the similar case search apparatus 100.

In the target image input processing, for example, the CPU 101 receives an image to be stored from the medical image database 130 via the LAN 150, as described above. Alternatively, the CPU 101 reads out an image to be stored from one of a storage device connected to the similar case search apparatus 100 and various storage media such as an FDD, CD-RW drive, MO drive, and ZIP drive.

In step S202, the CPU 101 selects medical record data corresponding to the image to be stored from the medical record database 140. In the medical record data selection processing, medical record data having the same case data ID as a case data ID accessory to the image to be stored is extracted from the medical record database 140.

In step S203, the CPU 101 extracts case data of the same patient as that of the image to be stored from the case database 120. In the case data extraction processing, case data having the same case data ID as a case data ID accessory to the image to be stored are extracted from the case database 120. A flag New is defined to represent whether the image to be stored is new case data. When the case data are extracted from the case database 120, New=F is set. If no case data is extracted, the image to be stored is regarded as new case data, and the flag New=T is set.

In step S204, the CPU 101 recognizes a morbid region from the image to be stored. In the morbid region recognition processing, the CPU 101 displays the image to be stored on the monitor 111 and stores a region designated by an image interpreter in the main memory 102.

More specifically, the main memory 102 stores the number of a slice (to be referred to as a slice of interest) which is designated by operating the mouse 112 because the image interpreter determines that this slice most properly visualizes a morbid region. The main memory 102 also stores the coordinates of a region of interest in the slice of interest.

The monitor 111 displays past case data closest in imaging period to the image to be stored among the case data extracted in step S203. Further, the monitor 111 displays the region of interest of the morbid portion. At this time, the image interpreter designates a region of interest in the image to be stored that represents the same morbid portion as the region of interest in the past case data. The main memory 102 stores the designated region of interest. As a result, the region of interest of the same morbid portion as the past case data is extracted from the image to be stored.

However, the processing of recognizing a morbid region from an image to be stored is not limited to this. For example, the CAD technique described in patent reference 1 may be adopted to automatically detect the position where a morbid portion exists by analyzing an image to be stored, and automatically set a region of interest containing the morbid portion without the mediacy of an image interpreter.

This processing is executed only when the flag New=F is set in step S203.

In step S205, the CPU 101 analyzes the image of the region of interest recognized in step S204, extracting an image feature amount representing the feature of the disease. For example, when the target disease (abnormality) is pulmonary nodule, each element $\{f_1, f_2, \ldots, f_n\}$ (n is the element number of the image feature amount) of an image feature amount vector F is the size of the nodule, the contrast difference between the inside and periphery of the nodule, the mean and variance of the internal density of the nodule, the complexity of the boundary of the nodule region, or the like.

In step S206, the CPU 101 associates the image to be stored with the medical record data extracted in step S202. Further, the CPU 101 associates the case data extracted in step S203, the morbid region recognized in step S204, and the image feature amount extracted in step S205.

In the association processing, the image to be stored, medical record data, morbid region, and image feature amount are associated with each other as one inspection data. If the flag New=F has been set in step S203, the imaging period of the image to be stored is compared with that of each image of the extracted case data. The inspection data including the image to be stored are added to the case data so that they are aligned in time series. Accordingly, medical image data are associated in time series in the case data having the same ID.

To the contrary, if New=T has been set, the image to be stored is new case data and is not associated with case data. The image to be stored is stored as new case data in the case database 120.

By this processing, case data as represented in the case data table of Table 1 are stored. Note that items such as the definite diagnosis name and the progress of a disease in Table 1 are acquired from medical record data.

<3. Disease Progress Model Building Function>

Details of the disease progress model building function will be explained with reference to the flowchart of FIG. 3. The progress pattern of a disease changes depending on the nature of a disease and the age group and sex of a patient. Thus, the similar case search apparatus 100 according to the first embodiment defines different groups (to be referred to as case groups) depending on the disease nature, patient's age group, and patient's sex. A disease progress model is built for each case group.

Table 2 exemplifies a case group defined for each disease nature, patient's age group, and patient's sex.

TABLE 2

| Case Group ID | Definite Diagnosis Name | Patient's Sex | Patient's Age Group |
|---|---|---|---|
| 1 | Diagnosis name 1 | Male | Earlier age |
| 2 | Diagnosis name 1 | Male | Middle age |
| 3 | Diagnosis name 1 | Male | Advanced age |
| 4 | Diagnosis name 1 | Female | Earlier age |
| 5 | Diagnosis name 1 | Female | Middle age |
| 6 | Diagnosis name 1 | Female | Advanced age |
| 7 | Diagnosis name 2 | Male | Earlier age |
| 8 | Diagnosis name 2 | Male | Middle age |
| 9 | Diagnosis name 2 | Male | Advanced age |
| 10 | Diagnosis name 2 | Female | Earlier age |
| 11 | Diagnosis name 2 | Female | Middle age |
| 12 | Diagnosis name 2 | Female | Advanced age |
| 13 | Diagnosis name 3 | Male | Earlier age |
| 14 | Diagnosis name 3 | Male | Middle age |

TABLE 2-continued

| Case Group ID | Definite Diagnosis Name | Patient's Sex | Patient's Age Group |
|---|---|---|---|
| 15 | Diagnosis name 3 | Male | Advanced age |
| 16 | Diagnosis name 3 | Female | Earlier age |
| 17 | Diagnosis name 3 | Female | Middle age |
| 18 | Diagnosis name 3 | Female | Advanced age |
| ... | ... | ... | ... |

When building a disease progress model for each case group, respective case data stored in the case database 120 are classified into the above-mentioned case groups. For each case group, a pattern is attained by averaging the time-series progress patterns of respective case data belonging to the group. The pattern is defined as a disease progress model.

To obtain the average model of a plurality of case data, time-series medical image data of the case data need to be made to correspond to each other in the same coordinate system. In the first embodiment, time-series medical image data of case data are made to correspond to each other on the same temporal axis based on the stage of a disease. The sequence of these processes will be explained with reference to the flowchart of FIG. 3.

In step S301, the CPU 101 creates discrete time-series data of an image feature amount from the image feature amounts of time-series medical image data in each case data in the case database 120.

In this case, elements are made to correspond to each other between a plurality of image feature amount vectors F in each case data. The image feature amount vector of each medical image data in given case data is defined as $F_k = \{f_1^k, f_2^k, \ldots, f_n^k\}$.

k is the number of the image feature amount vector of each medical image data, and n is the number of the element of the image feature amount vector. At this time, $F_k$ elements are made to correspond to each other between all medical image data contained in the same case data. For example, for the first element of the image feature amount in case data having a case data ID of 1 in Table 1, five vectors $f_1^1, f_1^2, f_1^3, f_1^4$, and $f_1^5$ are made to correspond to each other. The remaining elements are also similarly made to correspond to each other.

For each element after correspondence, a coordinate system is built by plotting the time along the abscissa axis and the image feature amount value along the ordinate axis. Image feature amounts plotted in this coordinate system are defined as discrete time-series data of each element.

Figure 4:
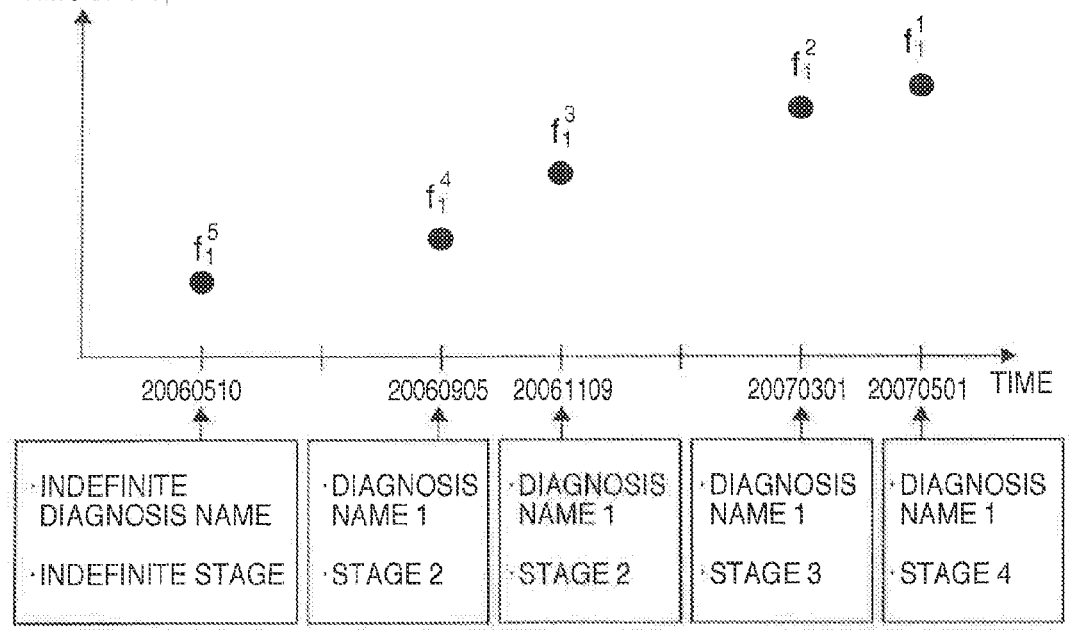
FIG. 4 is a graph of discrete time-series data.

FIG. 4 is a graph of discrete time-series data of the first element of the image feature amount. The processing in step S301 is done for all case data stored in the case database 120.

In step S302, the CPU 101 classifies discrete time-series data in each case data that have been created in step S301, into one of the case groups represented in Table 2.

For example, case data having "definite diagnosis name: diagnosis name 1", "patient's sex: male", and "patient's age group: advanced age" is classified into "case group ID: 3". The processing in step S302 is performed for all case data stored in the case database 120.

In step S303, the CPU 101 sets the total number of case groups to N and the target case group ID: i to 1.

In step S304, the CPU 101 makes all discrete time-series data belonging to the target case group ID: i (to be referred to as group ID: i) correspond to each other on the same coordinate axis. The processing in step S304 will be exemplified below. However, the discrete time-series data correspondence processing is not limited to the following method.

As shown in FIG. 4, if a diagnosis name is finalized at each time point of discrete time-series data, the stage of the disease is also finalized. Based on the stage of the disease, discrete time-series data are made to correspond to each other.

More specifically, $D_A$ and $D_B$ are two discrete time-series data to each of which the stage of a disease is assigned on the time axis. Each of $P_A$ and $P_B$ is a set of stages (five stages in this example) of a disease assigned to a corresponding one of $D_A$ and $D_B$ on the time axis. Note that there are as many $P_A$ and $P_B$ values as diagnosed cases in the respective time-series data. At this time, $D_B$ is translated to $D_A$ only along the time axis. The translation stops at a position where the positions of $P_A$ and $P_B$ values come closest to each other, thereby aligning $D_A$ and D.

Consequently, $D_A$ and $D_B$ are made to correspond to each other to bring respective stages of diseases closest to each other. This correspondence processing is executed between all discrete time-series data belonging to the group ID: i.

In step S305, the CPU 101 creates a disease progress model based on discrete time-series data belonging to the group ID: i that have been made to correspond to each other on the same coordinate axis in step S304.

More specifically, the CPU 101 creates a disease progress model pattern by applying the least-squares method to all discrete time-series data points plotted on the same coordinate axis. The disease progress model is created for each element $\{f_1, f_2, \ldots, f_n\}$ of the image feature amount vector F. Further, a vector $M_i = \{M_1^i, M_2^i, \ldots, M_n^i\}$ of the disease progress model having the group ID: i is defined.

Figure 5:
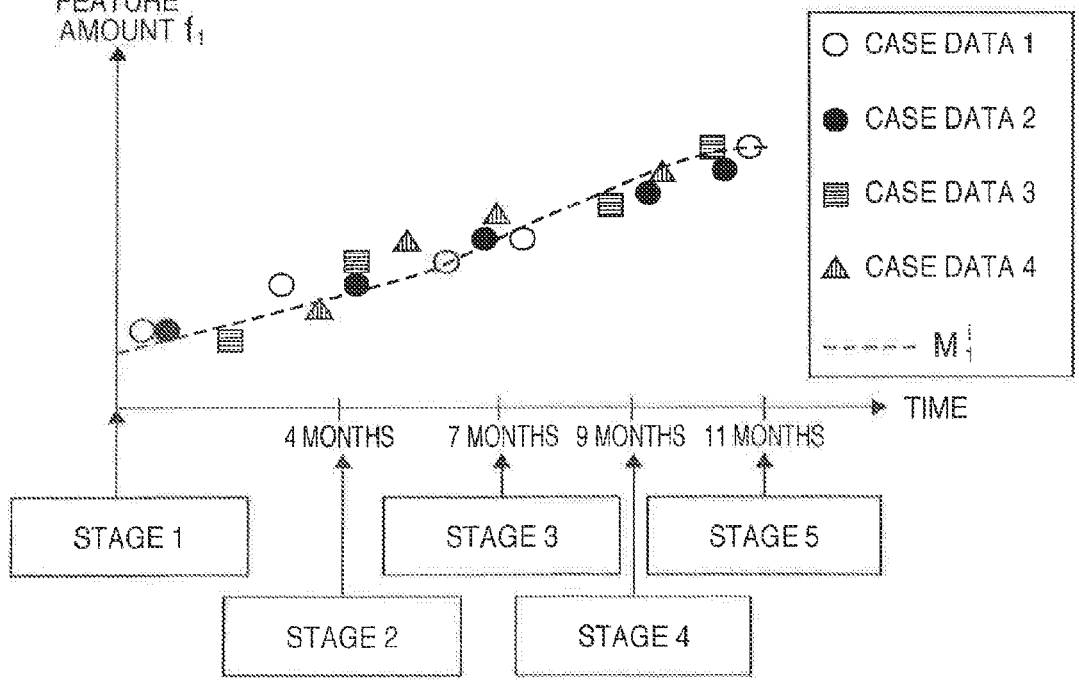
FIG. 5 is a graph showing a disease progress model.

FIG. 5 is a graph showing a disease progress model $M_1^i$ (curve indicated by a dotted line) obtained by applying the least-squares method to discrete time-series data of the image feature amount $f_1$ for four case data belonging to the group ID: i that are plotted on the same coordinate axis.

In step S306, the CPU 101 saves the vector $M_i$ of the disease progress model obtained in step S305. $M_i$ may be saved in the case database 120 or magnetic disk 103.

In step S307, the CPU 101 increments the value of the group ID: i by one.

In step S308, the CPU 101 checks the value of the group ID: i. If the i value is equal to or smaller than the total number N of case groups, the process returns to step S304; if NO, the disease progress model building processing ends.

By this processing, the disease progress model of each case group is built. After building the disease progress model of each case group, the similar case search function can be executed.

<4. Similar Case Search Function>

Details of the similar case search function will be described with reference to the flowchart of FIG. 6.

Figure 3:
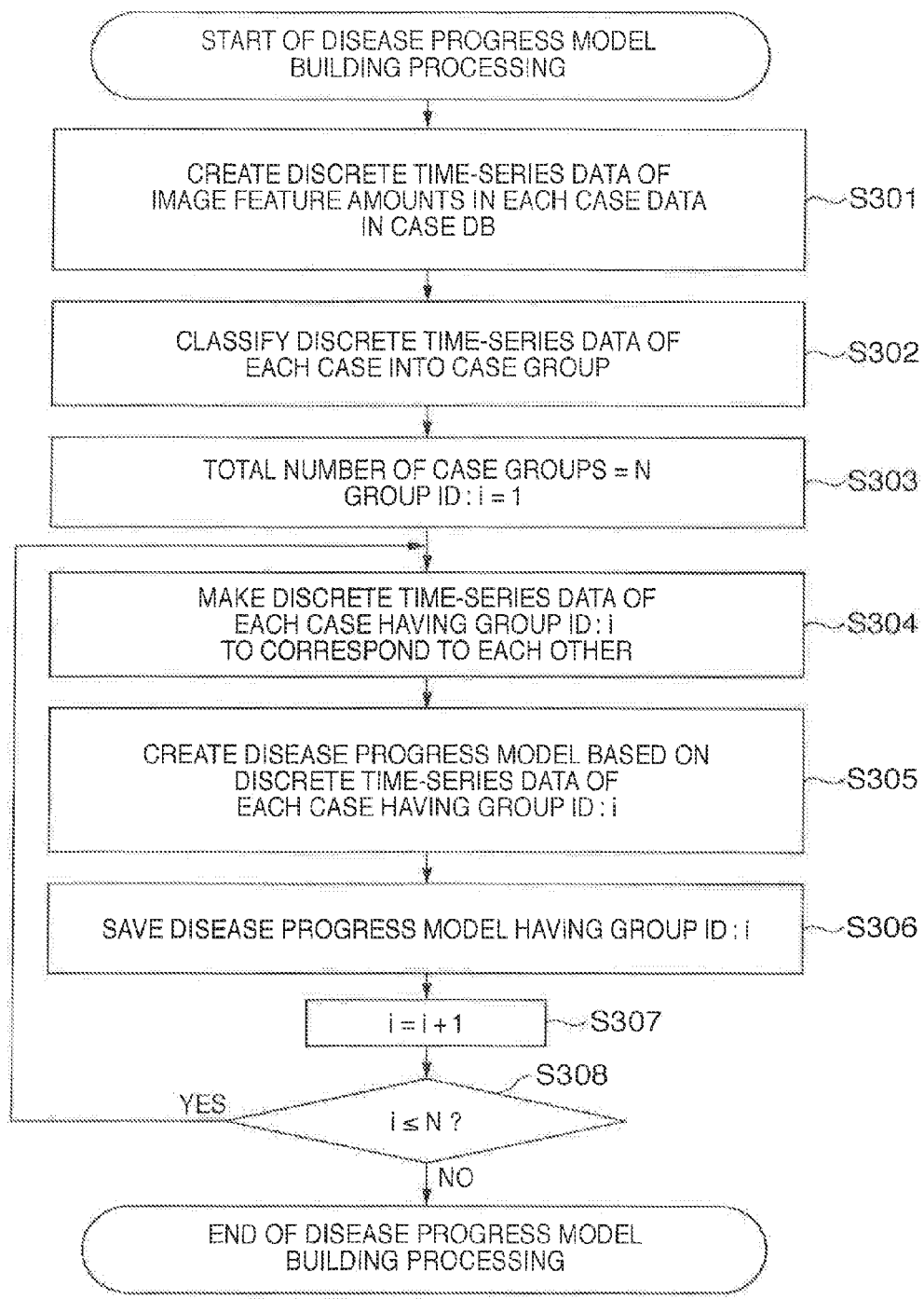
FIG. 3 is a flowchart showing the sequence of disease progress model building processing.

The first embodiment interpolates discrete time-series data by applying a disease progress model generated by executing the disease progress model building processing in FIG. 3 to discrete time-series data of the image feature amount of a case to be inspected.

Then, the interpolated discrete time-series data is compared with discrete time-series data of each case data in the case database 120, calculating the similarity between them. With the interpolated discrete time-series data, the similarity between the case to be inspected and discrete time-series data at an arbitrary imaging time interval can be calculated.

Case data similar to the case to be inspected are selected based on the calculated similarity, and presented in time series. This processing will be explained in detail with reference to the flowchart.

In step S601, the CPU 101 reads out an image to be inspected from the medical image database 130 in accordance with an input from the mouse 112 or keyboard 113. The CPU 101 inputs the readout image to the similar case search apparatus 100. The input processing is the same as step S201 of FIG. 2, and a detailed description thereof will not be repeated.

In step S602, the CPU 101 extracts case data of the same patient as that of the image to be inspected from the case database 120, and associates time-series medical image data contained in the extracted case data. At this time, the case database 120 is assumed to have stored in advance case data of the same patient as that of the image to be inspected.

Figure 2:
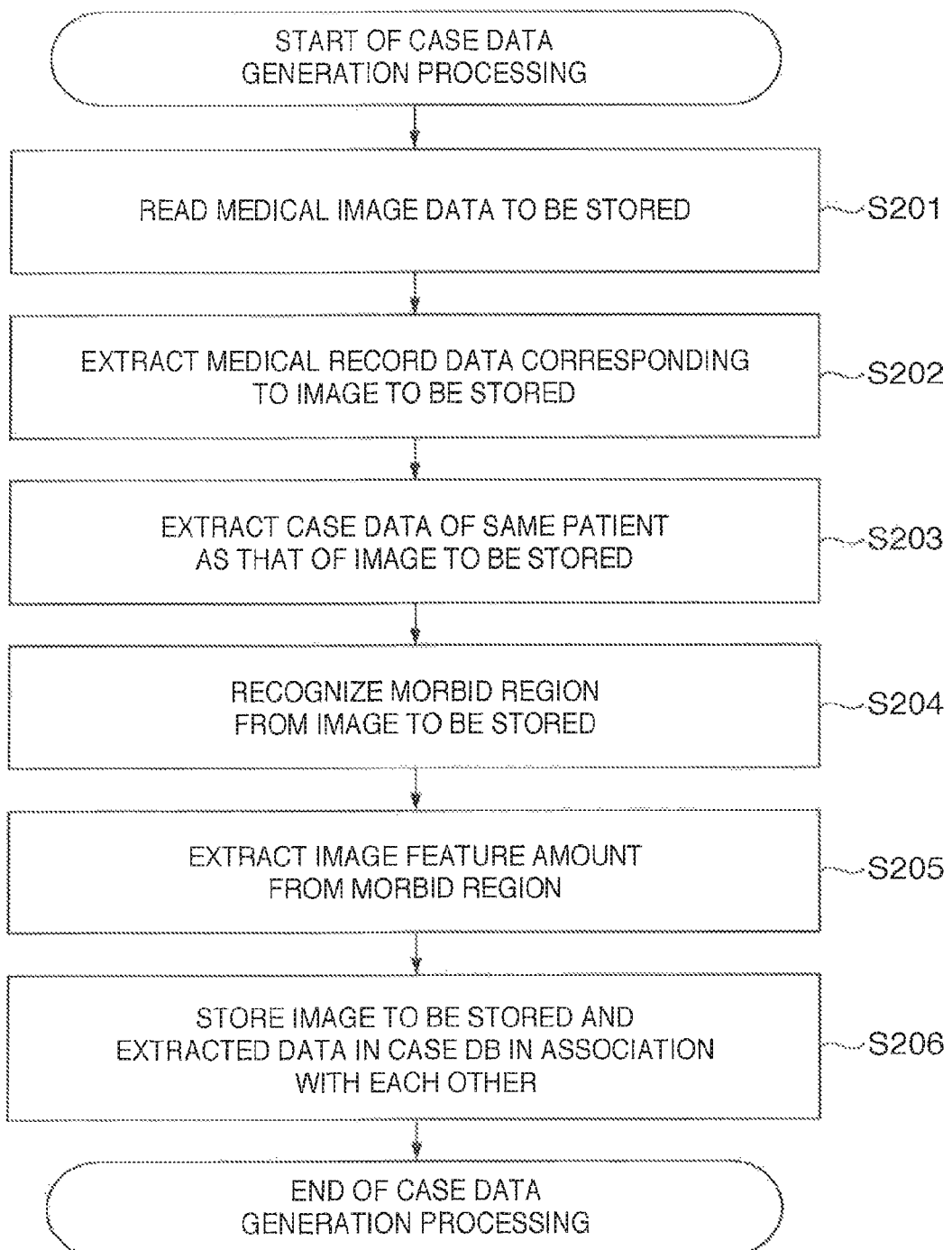
FIG. 2 is a flowchart showing the sequence of case data generation processing.

The case data extraction processing in the association processing is the same as the processes in steps S202 to S205 of FIG. 2, so a detailed description thereof will not be repeated. During the association processing, the morbid region of the image to be inspected is recognized, and an image feature amount is extracted. The extracted case data and the image to be inspected are associated with each other based on the case data ID.

Table 3 represents the result of associating an image to be inspected and extracted case data. As represented in Table 3, the extracted case data contains morbid regions and image feature amounts in time-series medical image data of the same patient imaged in the past. Hence, these pieces of information on time-series medical image data of the same patient as that of the image to be inspected are associated as a case to be inspected.

male", and "patient's age group: advanced age", the vector $M_3$ of a disease progress model corresponding to "case group ID: 3" is selected. The selected disease progress model is applied to discrete time-series data of the case to be inspected.

FIG. 8 shows an example in which discrete time-series data $d_1^T$ of a case to be inspected for an image feature amount $f_1$ is interpolated by applying a disease progress model $M_1^3$ to $d_1^T$. Note that $d_1^T$: $\{f_1^{19}, f_1^{18}, f_1^{17}, f_1^{16}, f_1^{7}\}$.

This processing is executed by the following procedures (but the interpolation processing based on a disease progress model is not limited to the following method).

First, the disease progress model $M_1^3$ is divided at a plurality of control points and approximated by a spline curve $C_1$. In this case, a division interval a is set to $\frac{1}{10}$ of the entire time of discrete time-series data.

Then, the discrete time-series data $d_1^T$ of a case to be inspected and the curve $C_1$ are aligned by the same processing as step S304 of FIG. 3.

Several control points on the curve $C_1$ are replaced with points on $d_1^T$ to redraw a spline curve $C_1^t$. For example, control points falling within a predetermined distance ($\alpha$ is applied in this example) from each point $f_1^k$ contained in $d_1^T$ are replaced with points $f_1^k$.

Based on an average disease progress model, unique successive time-series data containing the discrete time-series data $d_1^T$ are created. These data are called interpolated time-

TABLE 3

| Case Data ID (Patient ID) | Definite Diagnosis Name | Stage of Disease | Refrence Information to Material Record Data | Imaging Date | Image Type | Target Organ | Reference Information to Image Data | Slice Number of Interest | Coordinate Information of Region of Interest (X0, Y0, X1, Y1) | Image Statistical Data F of Region of Interest |
|---|---|---|---|---|---|---|---|---|---|---|
| Inspection Target | 4 | Undiagnosed | ... | 20070601 | Contrast enhanced CT | Lung | ... | 45 | (173, 152, 235, 268) | Ft |
| Extracted Case Data | 4. | Diagnosis name 1 | 4 ... | 20070314 | Contrast enhanced CT | Lung | ... | 42 | (171, 158, 241, 262) | F16 |
| | | Diagnosis name 1 | 3 ... | 20061205 | Contrast enhanced CT | Lung | ... | 46 | (169, 155, 237, 264) | F17 |
| | | Diagnosis name 1 | 2 ... | 20060812 | Contrast enhanced CT | Lung | ... | 43 | (167, 156, 239, 263) | F18 |
| | | Indefinite | ... | 20060510 | Contrast enhanced CT | Lung | ... | 44 | (168, 154, 236, 265) | F19 |

In step S603, the CPU 101 creates discrete time-series data from the image feature amounts in the time-series medical image data of the case to be inspected that have been associated in step S602. More specifically, an image feature amount $F_t$ of the image to be inspected in Table 2 is defined as $F_t=\{f_1^t, f_2^t, \ldots, f_n^t\}$. By the same processing as step S301 of FIG. 3, $F_t$ and the image feature amount vector $F_k$ of each medical image data in the extracted case data are made to correspond to each other for each element.

FIG. 7 is a graph showing discrete time-series data of the first image feature amount after the correspondence.

In step S604, the CPU 101 interpolates the discrete time-series data to be inspected based on the disease progress model. The CPU 101 first classifies the case to be inspected into a case group in Table 2, and then selects a disease progress model corresponding to the case group. As a result, a disease progress model best matching the case to be inspected is selected.

The disease progress model is selected from the case database 120 when stored in the case database 120, and from the magnetic disk 103 when stored in the magnetic disk 103.

For example, when the case to be inspected belongs to "definite diagnosis name: diagnosis name 1", "patient's sex:

series data of the case to be inspected for the image feature amount $f_1^k$, and represented by data $q_1^T$. The same processing is also performed for the remaining image feature amounts $f_2, \ldots, f_n$, creating an interpolated time-series data vector $Q_T=\{q_1^T, q_2^T, \ldots, q_n^T\}$.

In step S605, the CPU 101 calculates the similarity between the interpolated time-series data of the case to be inspected that have been created in step S604 and discrete time-series data of each case data stored in the case database 120.

In the similarity calculation processing, similar to step S304 of FIG. 3, the interpolated time-series data of the case to be inspected and discrete time-series data of the case data ID: i to be compared are aligned on the same time axis so that respective stages of diseases in these data come closest to each other.

The vector of discrete time-series data of the case data ID: i will be called $Di=(d_1^i, d_2^i, \ldots, d_n^i)$.

A method of calculating similarity $S_i$ between data $Q_T$ and data $D_i$ will be exemplified. However, the method of calculating the similarity $S_i$ is not limited to the following one.

The data $Q_T$ is successive time-series data and contains data corresponding to respective time points of the discrete time-series data $D_i$ on the time axis. Discrete time-series data obtained by plotting data at the same time points as discrete time points in the data $D_i$ are extracted and defined as $Q'_T = \{q'^T_1, q'^T_2, \ldots, q'^T_n\}$.

The data $Q'_T$ and data $D_i$ have data at the same discrete time points. By comparing the image feature amounts of the data $Q'_T$ and data $D_i$ at respective time points, image feature amounts having no time difference can be compared.

Discrete time points of the data $D_i$ are defined as $p_1, p_2, \ldots, p_m$ (m is the sum of discrete points). $F_{T,pj}$ and $F_{i,pj}$ are the image feature amount vectors of $Q'_T$ and $D_i$ at a given time point $p_j$ ($1 \le j \le m$). Equation (1) is an example of an equation for calculating similarity $s_{i,pj}$ between $F_{T,pj}$ and $F_{i,pj}$:

[Mathematical 1]

$$s_{i,pj} = \frac{1}{1 + \sqrt{(F_{T,pj} - F_{i,pj})^2}} \quad (1)$$

Equation (2) is an example of an equation for calculating similarity $S_i$ in time series:

[Mathematical 2]

$$S_i = \frac{\sum_{j=1}^{m} s_{i,pj}}{m} \quad (2)$$

In this case, the average value of the similarity $s_{i,pj}$ at each time point is set as the similarity $S_i$ in time series. Similarities between the remaining case data stored in the case database 120 and the case to be inspected are also calculated by the same method.

In step S606, the CPU 101 selects case data similar to the case to be inspected, based on the similarity calculated in step S605. In the first embodiment, a plurality of case data (constant b) are selected in descending order of similarity with the case to be inspected. For example, b=5 is applied, and five case data are selected.

In step S607, the CPU 101 presents, in time series, the case data (similar case data) which are similar to the case to be inspected and have been selected in step S606.

Figure 9A:
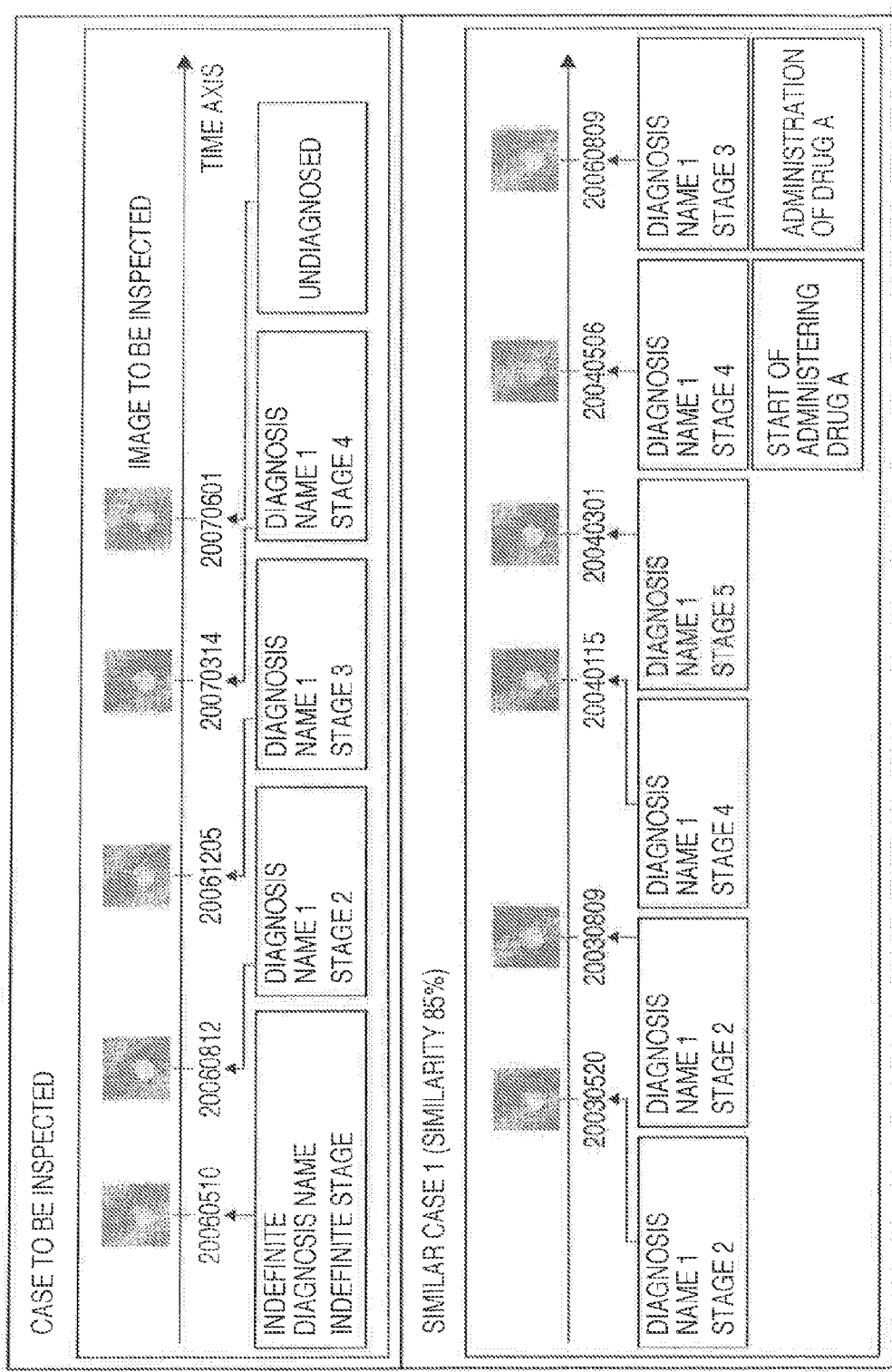
FIG. 9A is a view exemplifying a similar case data presentation method.
Figure 9B:
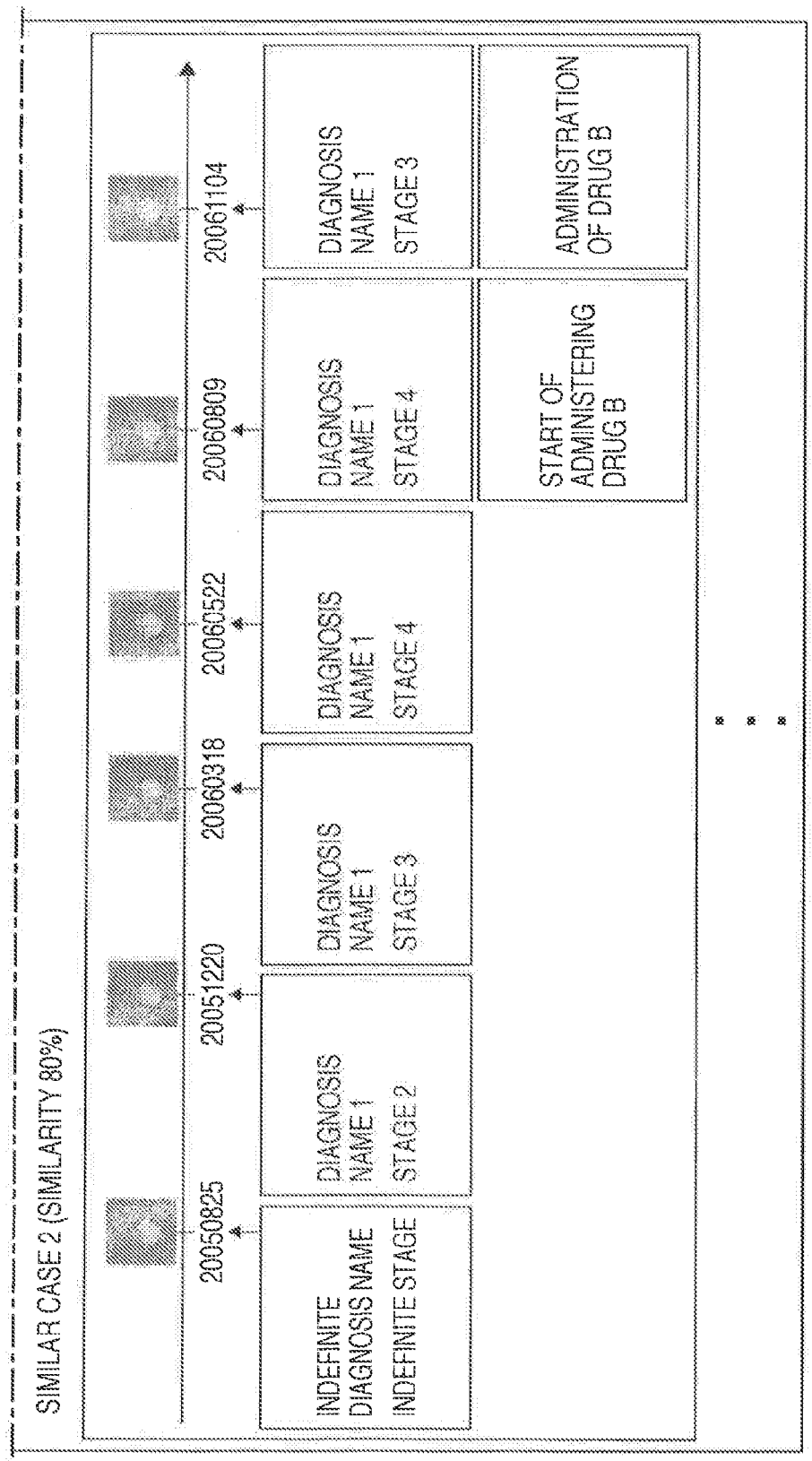
FIG. 9B is a view exemplifying the similar case data presentation method.

FIGS. 9A and 9B are views exemplifying a similar case data presentation method in the first embodiment. As shown in FIGS. 9A and 9B, the abscissa represents the time axis. Time-series images of interest of a morbid portion in a case to be inspected are arranged above the time axis. At this time, the imaging date and time, the diagnosis name, and the stage of a disease are also arranged. Similar case data aligned in step S605 are displayed in the same way in descending order of similarity. If a medical treatment has been done for selected similar case data, the medical treatment method is also displayed.

As is apparent from the above description, the similar case search apparatus according to the first embodiment calculates similarity using interpolated time-series data obtained by interpolating the discrete values of time-series image feature amounts.

The similar case search apparatus can present even similar case data which is different in imaging time interval and inspection time interval from a case to be inspected but exhibits a similar progress.

The similar case search apparatus according to the first embodiment also presents an inspection and medical treatment given to a patient corresponding to similar case data. The similar case search apparatus can provide not only information useful for diagnosing a case to be inspected but also information helpful for policymaking by an image interpreter when examining an inspection policy and treatment policy.

Modification 1 to First Embodiment

The disease progress model building processing described with reference to FIG. 3 may be executed based on statistical data when the progress pattern of a disease, which changes depending on, for example, the nature of a disease and the sex and age of a patient, has been known statistically.

Modification 2 to First Embodiment

In the similar case data selection processing in step S606 of FIG. 6, similar case data is presented based on the similarity of an image feature amount change pattern. Instead, similar case data may be presented based on, for example, comparison with another clinical information.

Information on the sex and age of a patient is considered when classifying a case to be inspected and case data in the case database 120 into case groups. As other kinds of clinical information, the past history, smoking history, and genetic information of a patient may be taken into account when narrowing similar case data.

The past history and smoking history of a patient are likely to be correlated to a definite diagnosis name, and genetic information is likely to be correlated to the effects of a drug. Selected case data are narrowed down to case data having these kinds of information matching those of a case to be inspected, thereby increasing the similar case data search precision.

Modification 3 to First Embodiment

In the processing of presenting similar case data in time series in step S607 of FIG. 6, for example, at least one image feature amount highly correlated to a change of the stage of a disease may be selected to present discrete time-series data of the image feature amount.

For example, when a disease to be inspected is pulmonary nodule, a change of the stage of the disease is highly correlated to a change of the size of the pulmonary nodule. Thus, discrete time-series data representing a change of the size of the pulmonary nodule in similar case data are presented. An image interpreter can predict a future change of the size of the pulmonary nodule in the case to be inspected.

Second Embodiment

In the first embodiment, disease progress models are classified by the disease nature, patient's age group, and patient's sex. However, the present invention is not limited to this.

Generally when a disease is treated, it follows a different progress pattern depending on the treatment. In the second embodiment, a case group (to be referred to as a prognosis case group) after the start of a treatment (to be referred to as prognosis) is newly defined. A corresponding progress pattern model (to be referred to as a treatment progress model) is built.

The overall configuration of a medical information system and the arrangement of a similar case search apparatus in the second embodiment are the same as those in the first embodiment, and a description thereof will not be repeated. A disease progress model before the start of a treatment (to be referred to as pretreatment) is built by the same method as that in the first embodiments, and a description thereof will not be repeated.

Table 4 exemplifies a prognosis case group. The progress of a disease after treatment depends on that of a disease before treatment. The prognosis case group is therefore defined by subdividing the pretreatment case group. For example, a pretreatment case group ID: 1 is subdivided into prognosis case group IDs: 1 to 6.

TABLE 4

| Prognosis Case Group ID | Pretreatment Case Group ID | Execution/ Non-execution of Operation | Administered Drug |
|---|---|---|---|
| 1 | 1 | ○ | Drug A |
| 2 | 1 | ○ | Drug B |
| 3 | 1 | ○ | Drug C |
| 4 | 1 | X | Drug A |
| 5 | 1 | X | Drug B |
| 6 | 1 | X | Drug C |
| 7 | 2 | ○ | Drug A |
| 8 | 2 | ○ | Drug B |
| 9 | 2 | ○ | Drug C |
| 10 | 2 | X | Drug A |
| 11 | 2 | X | Drug B |
| 12 | 2 | X | Drug C |
| 13 | 3 | ○ | Drug A |
| 14 | 3 | ○ | Drug B |
| 15 | 3 | ○ | Drug C |

TABLE 4-continued

| Prognosis Case Group ID | Pretreatment Case Group ID | Execution/ Non-execution of Operation | Administered Drug |
|---|---|---|---|
| 16 | 3 | X | Drug A |
| 17 | 3 | X | Drug B |
| 18 | 3 | X | Drug C |
| ... | ... | ... | ... |

For "non-execution of an operation", the state of a disease changes continuously depending on medication. Thus, the treatment progress model is built based on the flowchart of FIG. 3, as well as a disease progress model before treatment.

For "execution of an operation", the state of a disease before an operation is the same as that for "non-execution of an operation". After the operation, a morbid portion is resected and the state of the disease greatly changes. Hence, for "execution of an operation", a treatment progress model (to be referred to as a postoperative treatment progress model) is built based on postoperative discrete time-series data of case data. A treatment progress model for "non-execution of an operation" will be called a preoperative treatment progress model to discriminate it from the postoperative treatment progress model.

In the second embodiment, case data stored in a case database 120 are case data obtained by adding an item regarding a treatment situation (one of pretreatment, start of treatment, and prognosis) to case data described in the first embodiment.

Table 5 exemplifies a case data table stored in the case database 120 in the second embodiment.

TABLE 5

| Case Data ID (Patient ID) | Definite Diagnosis Name | Stage of Disease | Pretreatment/ Start of Treatment/ Prognosis | Reference Information to Medical Record Data | Imaging Date | Image Type | Target Organ | Reference Information to Image Data | Slice Number of Interest | Coordinate Information of Region of Interest (X0, Y0, X1, Y1) | Image Feature Amount Fk of Region of Interest |
|---|---|---|---|---|---|---|---|---|---|---|---|
| 1 | Diagnosis name 1 | 1 | Prognosis | ... | 20070501 | Contrast enhanced CT | Lung | ... | 21 | (112, 263, 193, 335) | F1 |
| | Diagnosis name 1 | 2 | Prognosis | ... | 20070301 | Contrast enhanced CT | Lung | ... | 23 | (115, 260, 195, 340) | F2 |
| | Diagnosis name 1 | 3 | Start of treatment | ... | 20070109 | Contrast enhanced CT | Lung | ... | 26 | (110, 258, 188, 343) | F3 |
| | Diagnosis name 1 | 2 | Pretreatment | ... | 20070905 | Contrast enhanced CT | Lung | ... | 22 | (113, 262, 190, 338) | F4 |
| | Indefinite | | Pretreatment | ... | 20070510 | Contrast enhanced CT | Lung | ... | 22 | (112, 260, 186, 341) | F5 |
| 2 | Diagnosis name 6 | 5 | Prognosis | ... | 20070512 | Contrast enhanced CT | Lung | ... | 52 | (167, 258, 205, 292) | F6 |
| | Diagnosis name 6 | 5 | Prognosis | ... | 20070210 | Contrast enhanced CT | Lung | ... | 57 | (170, 248, 209, 295) | F7 |
| | Diagnosis name 6 | 4 | Start of treatment | ... | 20071106 | Contrast enhanced CT | Lung | ... | 54 | (171, 251, 208, 290) | F8 |
| | Diagnosis name 6 | 4 | Pretreatment | ... | 20070706 | Contrast enhanced CT | Lung | ... | 50 | (166, 249, 210, 293) | F9 |
| 3 | Diagnosis name 3 | 1 | Prognosis | ... | 20070516 | Plain CT | Lung | ... | 17 | (310, 219, 335, 254) | F10 |
| | Diagnosis name 3 | 2 | Prognosis | ... | 20070410 | Plain CT | Lung | ... | 19 | (315, 222, 340, 250) | F11 |
| | Diagnosis name 3 | 2 | Prognosis | ... | 20070315 | Plain CT | Lung | ... | 21 | (308, 215, 334, 259) | F12 |
| | Diagnosis name 3 | 3 | Start of treatment | ... | 20070108 | Plain CT | Lung | ... | 20 | (312, 225, 334, 248) | F13 |
| | Diagnosis name 3 | 2 | Pretreatment | ... | 20061125 | Plain CT | Lung | ... | 19 | (307, 212, 340, 251) | F14 |
| | Indefinite | | Pretreatment | ... | 20060812 | Plain CT | Lung | ... | 18 | (313, 218, 336, 253) | F15 |
| ... | ... | ... | ... | ... | ... | ... | ... | ... | ... | ... | ... |

<2. Similar Case Search Function>

The sequence of similar case search processing in a similar case search apparatus 100 according to the second embodiment will be explained with reference to the flowchart of FIG. 10.

In the second embodiment, discrete time-series data of a case to be inspected are divided into two, pretreatment data and prognosis data. The divided discrete time-series data are interpolated based on a disease progress model and treatment progress model, respectively. For each of the pretreatment data and prognosis data, the similarity between the interpolated data and case data in the case database 120 is calculated (first and second calculation units).

For each case data, total similarity is calculated based on both the similarities of the pretreatment data and prognosis data. Based on the calculated similarity, case data similar to the case to be inspected are selected and presented in time series. As for steps of performing the same processes as those in the flowchart of FIG. 6 in the first embodiment, only correspondences with the steps in FIG. 6 will be described and a detailed description thereof will not be repeated.

Processes in steps S1001 to S1003 are the same as those in steps S601 to S603 of FIG. 6. Processes in steps S1005 and S1006 are the same as those in steps S604 and S605.

In step S1004, a CPU 101 divides, into pretreatment data and prognosis data, discrete time-series data of the image feature amount of each case data that have been created in step S1003.

In step S1007, the CPU 101 interpolates, based on the above-mentioned treatment progress model, discrete time-series data (to be referred to as prognosis discrete time-series data) of the prognosis to be inspected.

More specifically, similar to step S604 of FIG. 6, the CPU 101 classifies the case to be inspected into a prognosis case group in Table 4, and selects a treatment progress model corresponding to the prognosis case group.

At this time, when the case to be inspected corresponds to "execution of an operation" and medication was done before the operation, a corresponding postoperative treatment progress model and a preoperative treatment progress model for the same medication are selected.

After that, the treatment progress model is applied to the discrete time-series data of the case to be inspected by the same processing as step S604. When both the preoperative and postoperative treatment progress models are selected, they are applied to preoperative prognosis discrete time-series data and postoperative prognosis discrete time-series data.

In step S1008, the CPU 101 calculates similarity $S_{post}$ between interpolated prognosis time-series data of the case to be inspected that has been created in step S1007, and discrete time-series data of each case data stored in the case database 120.

More specifically, the same processing as step S605 of FIG. 6 is done. When the interpolated prognosis time-series data are generated based on the two, preoperative and postoperative treatment progress models, the interpolated time-series data are divided into interpolated preoperative time-series data and interpolated postoperative time-series data. After the similarities of the respective interpolated time-series data are calculated, a value obtained by weighting and averaging these similarities according to equation (3) is defined as $S_{post}$:

[Mathematical 3]

$$S_{post} = u \cdot S_1 + (1-u) \cdot S_2 \quad (3)$$

where $S_1$ is the similarity of preoperative discrete time-series data, $S_2$ is the similarity of postoperative discrete time-series data, and u is a constant of a real number. In this case, u represents the ratio at which the time interval of preoperative prognosis discrete time-series data occupies prognosis time-series data of a case to be inspected.

In step S1009, the CPU 101 selects case data similar to the case to be inspected based on the pretreatment and prognosis similarities calculated in steps S1006 and S1008, respectively.

In the second embodiment, a value obtained by weighting and averaging the pretreatment similarity (to be referred to as $S_{pre}$) and the prognosis similarity $S_{post}$ is calculated as the total similarity of the same case data according to equation (4):

[Mathematical 4]

$$S_{all} = v \cdot S_{pre} + (1-v) \cdot S_{post} \quad (4)$$

where v is a constant of a real number. In this case, v represents the ratio at which the time interval of pretreatment time-series data occupies all discrete time-series data of a case to be inspected.

Similar to step S606 of FIG. 6, the CPU 101 selects a plurality of similar case data in descending order of the total similarity with the case to be inspected.

In step S1010, the CPU 101 presents, in time series, the similar case data selected in step S1009.

Figure 11A:
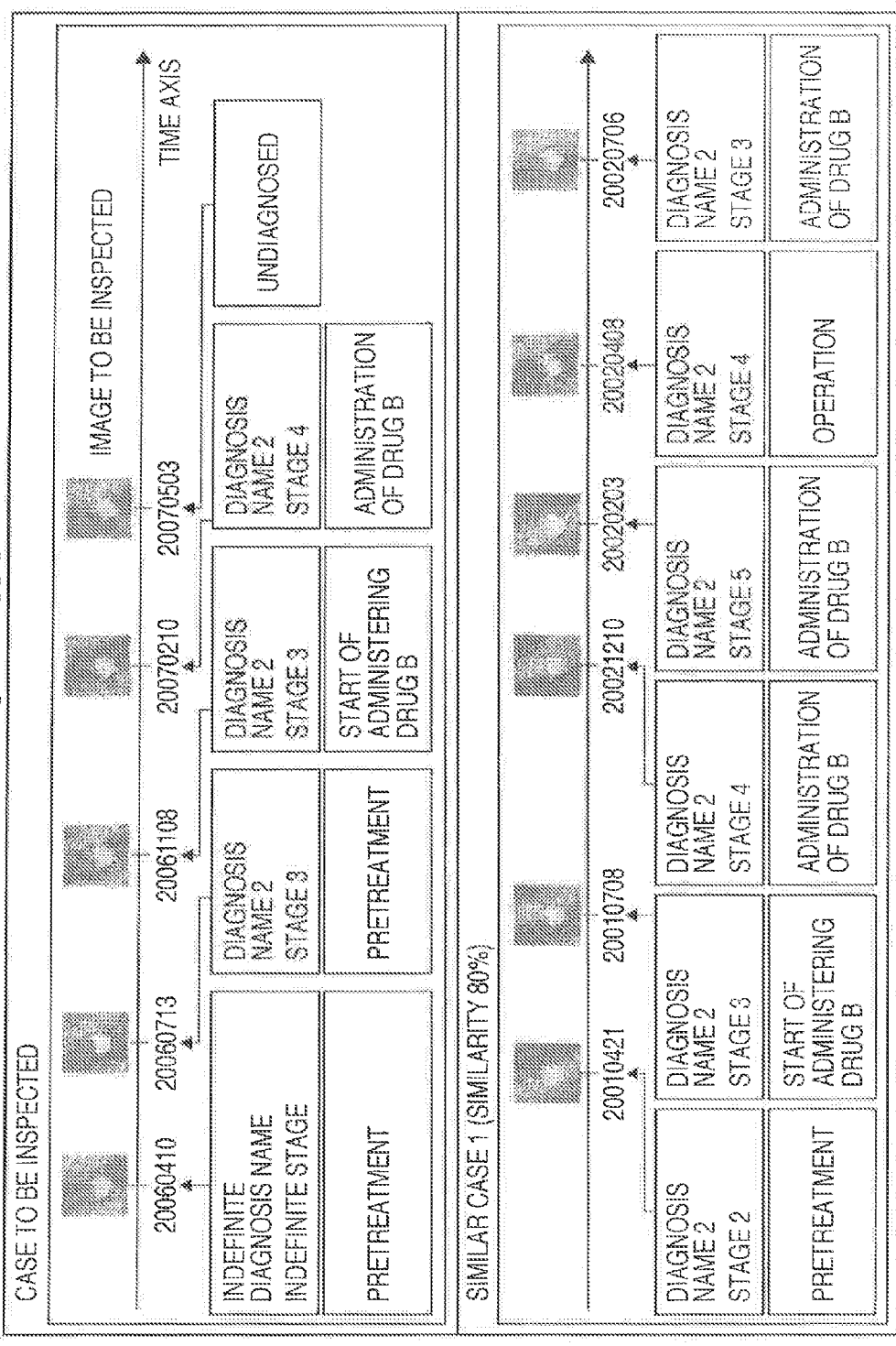
FIG. 11A is a view exemplifying a similar case data presentation method.
Figure 11B:
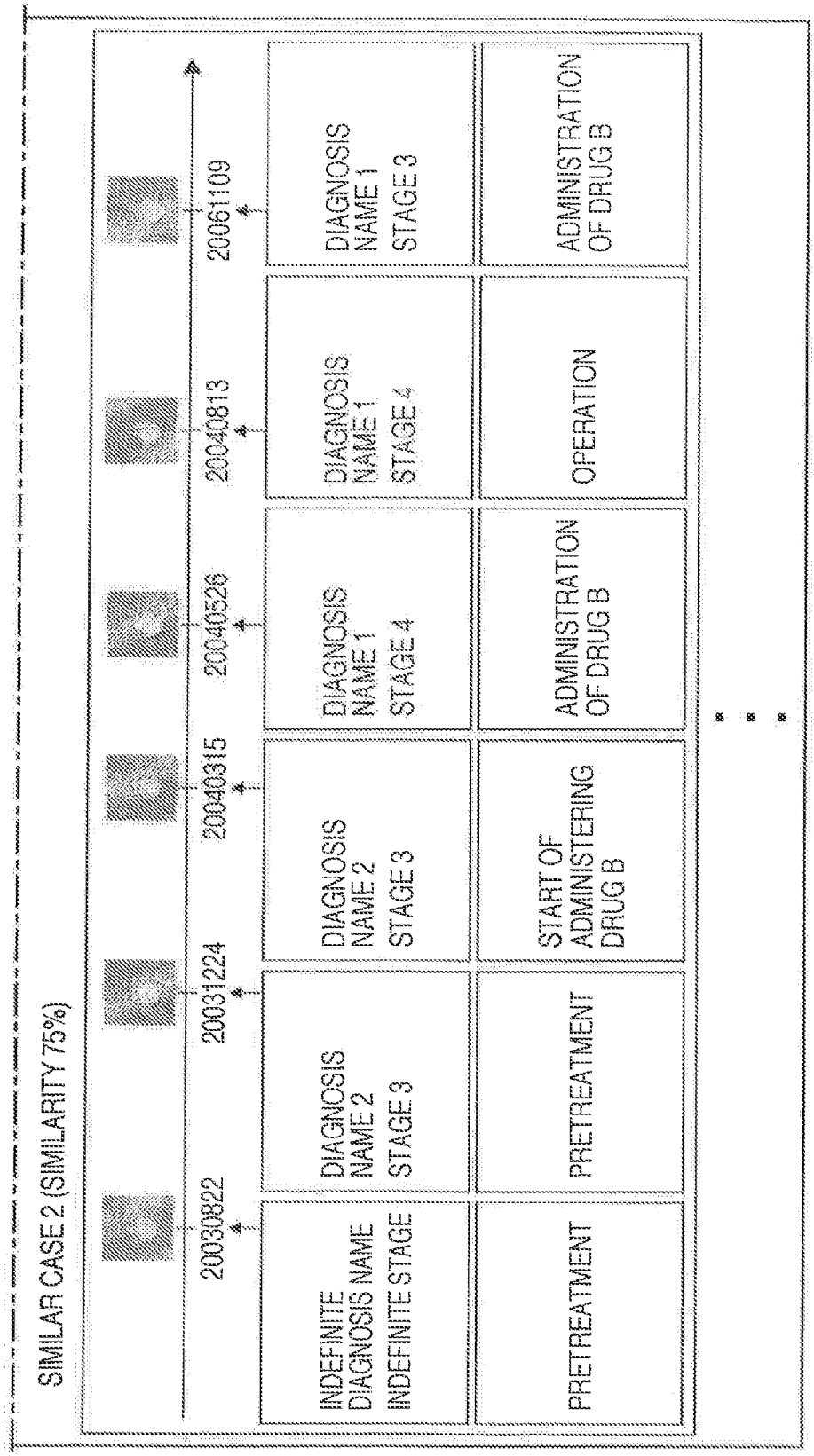
FIG. 11B is a view exemplifying the similar case data presentation method.

FIGS. 11A and 11B are views exemplifying a similar case data presentation method in the second embodiment. The display form in FIGS. 11A and 11B is the same as that in FIGS. 9A and 9B in the first embodiment. However, the display form in FIGS. 11A and 11B presents cases which are similar to a case to be inspected, which has already undergone a treatment, in the progress of a disease before the treatment and the progress of mediation before and after an operation (first and second output units).

As is apparent from the above description, the similar case search apparatus according to the second embodiment discriminates data before and after a treatment and before and after an operation, which change the progress of a disease. The similar case search apparatus interpolates discrete time-series data based on different disease progress models and separately calculates similarities.

For example, when discrete time-series data is interpolated based on only a pretreatment disease progress model for a case to be inspected which has already undergone a treatment, a mismatch occurs between the discrete time-series data and the pretreatment disease progress model. However, the similar case search apparatus according to the second embodiment can solve this problem.

If the pretreatment progress pattern of a case to be inspected is accidentally close to the prognosis progress pattern of case data stored in the case database 120, the case data is presented as one with high similarity though it is not similar case data originally. However, the similar case search apparatus according to the second embodiment can solve this problem.

Resultantly, the similar case search apparatus according to the second embodiment can more accurately interpolate discrete time-series data and calculate similarity.

Modification 1 to Second Embodiment

In step S1009, a specific number of similar case data are selected in descending order of total similarity calculated from pretreatment and prognosis similarities. However, the present invention is not limited to this. For example, a specific number of case data may be selected in descending order of each of pretreatment and prognosis similarities.

This method can present similar cases which pay attention to pretreatment and prognosis. This method is effective when an image interpreter wants to refer to a plurality of case data similar in only the progress of a disease before treatment so that he can confirm how the prognosis progresses of these case data differ from each other, and vice versa.

Further, the preoperative and postoperative similarities of prognosis data may be calculated separately to present similar case data which pay attention to pretreatment, pre-operation, and post-operation. Accordingly, this method can present similar case data similar in only process after an operation as a reference for treatment policymaking.

Modification 2 to Second Embodiment

In the second embodiment, when building a treatment progress model, case groups are created in accordance with treatment methods "execution/non-execution of an operation" and "administered drug", as represented in Table 4. However, treatment methods for classification into case groups are not limited to them.

Another treatment method which may affect the progress pattern of a disease is, for example, "radiotherapy". Depending on radiotherapy, case groups may be created. When presenting similar case data, information on "radiotherapy" may be presented as treatment information.

Third Embodiment

In the first and second embodiments, similarity is calculated by comparing interpolated time-series data obtained by interpolating discrete time-series data of a case to be inspected with discrete time-series data of case data in the case database 120. However, the present invention is not limited to this.

In contrast to the first and second embodiments, similarity may be calculated by comparing discrete time-series data of a case to be inspected with interpolated time-series data obtained by interpolating discrete time-series data of case data in a case database 120.

In this arrangement, discrete time-series data of case data in the case database 120 is interpolated in advance, and stored in a magnetic disk 103 easily accessible by a CPU 101 in similar case search. In similar case search, interpolated time-series data of each case data stored in the magnetic disk 103 is read out for comparison with discrete time-series data of a case to be inspected.

In this arrangement, interpolated time-series data of case data in the case database 120 is stored in advance in the magnetic disk 103. When executing similar case search, no interpolated time-series data need be created.

This can obviate the need to interpolate discrete time-series data of a case to be inspected in similar case search. The third embodiment can shorten the time of similar case search processing, as compared with the first and second embodiments.

Other Embodiments

The present invention is also achieved by executing the following processing. More specifically, software (program) for implementing the functions of the above-described embodiments is supplied to a system or apparatus via a network or various storage media. The computer (or the CPU or MPU) of the system or apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-006117, filed Jan. 14, 2009, which is hereby incorporated by reference herein in its entirety.

DESCRIPTION OF THE REFERENCE NUMERALS

100 similar case search apparatus
120 case database
130 medical image database
140 medical record database
150 LAN
110 controller

The invention claimed is:

1. An information processing apparatus comprising:
an interpolation unit configured to interpolate, by using an interpolation model, at least either of first feature amounts extracted from a plurality of medical images contained in case data and second feature amounts extracted from a plurality of medical images contained in inspection data;
a calculation unit configured to calculate similarities between the plurality of medical images contained in the inspection data and the plurality of medical images contained in the case data by comparing the first feature amounts with the second feature amounts on a display unit;
an output unit configured to output case data selected based on the calculated similarities; and
a display control unit configured to display an interpolated feature amount, the first feature amounts, and the second feature amounts,
wherein the interpolation unit generates, by performing interpolation based on at least either of the first feature amounts and the second feature amounts obtained by an imaging process in actual imaging periods, feature amounts at imaging periods that differ from the actual imaging periods of the medical images, and
wherein the display control unit displays the generated featured amounts, the first feature amounts, and the second feature amounts, which are aligned on a time axis on the display unit.

2. The information processing apparatus according to claim 1, further comprising a database which stores the case data containing a plurality of medical images obtained by imaging the same object in different periods,
wherein the case data to be used by the interpolation unit is read out from the database.

3. The information processing apparatus according to claim 1, wherein the interpolation unit interpolates the feature amounts by using the interpolation model selected based on at least one of a nature of a disease of an object, a sex of the object, an age of the object, and a treatment method of the disease.

4. The information processing apparatus according to claim 1, wherein the interpolation unit classifies the plurality of medical images into medical images obtained before treatment and medical images obtained after treatment, and interpolates feature amounts extracted from the respective medical images.

5. The information processing apparatus according to claim 4, wherein the calculation unit calculates similarities between the plurality of medical images contained in the inspection data and the plurality of medical images contained in the case data separately for the medical images obtained before treatment and the medical images obtained after treatment.

6. The information processing apparatus according to claim 4, wherein the calculation unit comprises:
a first calculation unit configured to calculate a similarity between the inspection data containing the medical images obtained before treatment and the case data containing the medical images obtained before treatment, and
a second calculation unit configured to calculate a similarity between the inspection data containing the medical images obtained after treatment and the case data containing the medical images obtained after treatment.

7. The information processing apparatus according to claim 6, wherein the output unit outputs case data selected based on a total similarity calculated using the similarity calculated by the first calculation unit and the similarity calculated by the second calculation unit.

8. The information processing apparatus according to claim 6, wherein the output unit comprises:
a first output unit configured to output case data selected based on the similarity calculated by the first calculation unit, and
a second output unit configured to output case data selected based on the similarity calculated by the second calculation unit.

9. An information processing method for an information processing apparatus, comprising:
interpolating, by using an interpolation model, at least either of first feature amounts extracted from a plurality of medical images contained in case data and second feature amounts extracted from a plurality of medical images contained in inspection data;
calculating similarities between the plurality of medical images contained in the inspection data and the plurality of medical images contained in the case data by comparing the first feature amounts with the second feature amounts;
outputting case data selected based on the calculated similarities; and
displaying an interpolated feature amount, the first feature amounts, and the second feature amounts,
wherein the first feature amounts and the second feature amounts are obtained by an imaging process in actual imaging periods,
wherein interpolating the at least either of the first feature amounts and the second feature includes generating feature amounts at imaging periods that differ from the actual imaging periods of the medical images, and
wherein the generated featured amounts, the first feature amounts, and the second feature amounts, which are aligned on a time axis, are displayed.

10. A non-transitory computer-readable storage medium storing a program for causing a computer to execute an information processing method, the method comprising:
interpolating, by using an interpolation model, at least either of first feature amounts extracted from a plurality of medical images contained in case data and second feature amounts extracted from a plurality of medical images contained in inspection data;
calculating similarities between the plurality of medical images contained in the inspection data and the plurality of medical images contained in the case data by comparing the first feature amounts with the second feature amounts;
outputting case data selected based on the calculated similarities; and
displaying an interpolated feature amount, the first feature amounts, and the second feature amounts,
wherein the first feature amounts and the second feature amounts are obtained by an imaging process in actual imaging periods,
wherein interpolating the at least either of the first feature amounts and the second feature includes generating feature amounts at imaging periods that differ from the actual imaging periods of the medical images, and
wherein the generated featured amounts, the first feature amounts, and the second feature amounts, which are aligned on a time axis, are displayed.

11. The apparatus according to claim 1, further comprising a building unit configured to build the interpolation model of temporal feature amount changes by extracting feature amounts from a plurality of medical images obtained by imaging the same object in different periods.

12. The method according to claim 9, further comprising building the interpolation model of temporal feature amount changes by extracting feature amounts from a plurality of medical images obtained by imaging the same object in different periods.

13. The non-transitory computer-readable storage medium according to claim 10, wherein the information processing method further comprises building the interpolation model of temporal feature amount changes by extracting feature amounts from a plurality of medical images obtained by imaging the same object in different periods.

14. An information processing apparatus comprising:
an interpolation unit configured to interpolate, by using an interpolation model, at least either of first feature amounts extracted from a plurality of time-series medical images contained in case data and second feature amounts extracted from a plurality of time-series medical images contained in inspection data;
a calculation unit configured to calculate similarities between the plurality of time-series medical images contained in the inspection data and the plurality of time-series medical images contained in the case data by comparing the first feature amounts with the second feature amounts;
an output unit configured to output case data selected based on the calculated similarities; and
a display control unit configured to display an interpolated feature amount, the first feature amounts, and the second feature amounts on a display unit,
wherein the interpolation unit generates, by performing interpolation based on at least either of the first feature amounts and the second feature amounts obtained by an imaging process in actual imaging periods, feature amounts at imaging periods that differ from the actual imaging periods of the medical images, and
wherein the display control unit displays the generated featured amounts, the first feature amounts, and the second feature amounts, which are aligned on a time axis on the display unit.

15. The apparatus according to claim 14, further comprising a building unit configured to build a temporal feature amount change model which is used as the interpolation model by the interpolation unit, by extracting feature amounts from a plurality of medical images obtained by imaging the same object in different periods.

16. An information processing method for an information processing apparatus, the method comprising:
    interpolating, by using an interpolation model, at least either of first feature amounts extracted from a plurality of time-series medical images contained in case data and second feature amounts extracted from a plurality of time-series medical images contained in inspection data;
    calculating similarities between the plurality of time-series medical images contained in the inspection data and the plurality of time-series medical images contained in the case data by comparing the first feature amounts with the second feature amounts;
    outputting case data selected based on the calculated similarities; and
    displaying an interpolated feature amount, the first feature amounts, and the second feature amounts,
    wherein the first feature amounts and the second feature amounts are obtained by an imaging process in actual imaging periods,
    wherein interpolating the at least either of the first feature amounts and the second feature amounts includes generating feature amounts at imaging periods that differ from the actual imaging periods of the medical images, and
    wherein the generated featured amounts, the first feature amounts, and the second feature amounts, which are aligned on a time axis, are displayed.

17. The method according to claim 16, further comprising building the interpolation model of temporal feature amount changes by extracting feature amounts from a plurality of medical images obtained by imaging the same object in different periods.

18. A non-transitory computer-readable storage medium storing a program for causing a computer to execute an information processing method, the method comprising:
    interpolating, by using an interpolation model, at least either of first feature amounts extracted from a plurality of time-series medical images contained in case data and second feature amounts extracted from a plurality of time-series medical images contained in inspection data;
    calculating similarities between the plurality of time-series medical images contained in the inspection data and the plurality of time-series medical images contained in the case data by comparing the first feature amounts with the second feature amounts;
    outputting case data selected based on the calculated similarities; and
    displaying an interpolated feature amount, the first feature amounts, and the second feature amounts,
    wherein the first feature amounts and the second feature amounts are obtained by an imaging process in actual imaging periods,
    wherein interpolating the at least either of the first feature amounts and the second feature amounts includes generating feature amounts at imaging periods that differ from the actual imaging periods of the medical images, and
    wherein the generated featured amounts, the first feature amounts, and the second feature amounts, which are aligned on a time axis, are displayed.

19. The non-transitory computer-readable storage medium according to claim 18, wherein the information processing method further comprises building the interpolation model of temporal feature amount changes by extracting feature amounts from a plurality of medical images obtained by imaging the same object in different periods.

* * * * *